(12) United States Patent
Chono et al.

(10) Patent No.: US 9,057,056 B2
(45) Date of Patent: Jun. 16, 2015

(54) METHOD FOR PRODUCING RETROVIRUS USING HUMAN PRODUCER CELLS WITH INCREASED N-ACETYLGLUCOSAMINYLTRANSFERASE III ACTIVITY

(75) Inventors: Hideto Chono, Otsu (JP); Hiromi Okuyama, Otsu (JP); Tomoe Egashira, Otsu (JP); Nobuto Koyama, Otsu (JP); Junichi Mineno, Otsu (JP); Ikunoshin Kato, Otsu (JP)

(73) Assignee: TAKARA BIO INC., Shiga (JP)

( * ) Notice: Subject to any disclaimer, the term of this patent is extended or adjusted under 35 U.S.C. 154(b) by 1136 days.

(21) Appl. No.: 11/663,990

(22) PCT Filed: Sep. 28, 2005

(86) PCT No.: PCT/JP2005/017875
§ 371 (c)(1),
(2), (4) Date: Mar. 28, 2007

(87) PCT Pub. No.: WO2006/035829
PCT Pub. Date: Apr. 6, 2006

(65) Prior Publication Data
US 2008/0293141 A1    Nov. 27, 2008

(30) Foreign Application Priority Data

Sep. 29, 2004  (JP) ................. 2004-283918

(51) Int. Cl.
*C12N 15/87* (2006.01)
*C12N 15/63* (2006.01)
*C12N 9/10* (2006.01)
*C12N 15/86* (2006.01)

(52) U.S. Cl.
CPC .............. *C12N 9/1051* (2013.01); *C12N 15/86* (2013.01); *C12N 2740/13043* (2013.01); *C12N 2740/13052* (2013.01); *C12N 2799/02* (2013.01); *C12N 2810/10* (2013.01)

(58) Field of Classification Search
CPC ................. C12N 9/1051; C12N 15/86; C12N 2740/13043; C12N 2740/13052; C12N 2799/02; C12N 2810/10; A61K 38/00
See application file for complete search history.

(56) References Cited

U.S. PATENT DOCUMENTS

| 5,470,726 | A | * | 11/1995 | Miller et al. ................. | 435/465 |
| 5,952,225 | A | * | 9/1999 | Pensiero et al. ............. | 435/352 |
| 6,033,907 | A | * | 3/2000 | Williams ..................... | 435/325 |
| 6,472,204 | B1 | | 10/2002 | Asada et al. | |
| 6,787,359 | B1 | | 9/2004 | Ueno et al. | |
| 2004/0058447 | A1 | | 3/2004 | Ueno et al. | |

FOREIGN PATENT DOCUMENTS

| WO | 9423048 | A2 | 10/1994 |
| WO | 9429440 | A1 | 12/1994 |
| WO | 9526200 | A1 | 10/1995 |
| WO | 9603520 | A1 | 2/1996 |

OTHER PUBLICATIONS

Savard et al., Defective herpes simplex virus type 1 vectors harboring gag, pol, and env genes can be used to rescue defective retrovirus vectors, J Virol. 71(5):4111-7, 1997.*
Proesmans et al., What's new in cystic fibrosis? From treating symptoms to correction of the basic defect. Eur J Pediatr. 167(8):839-49, 2008.*
Riordan, CFTR Function and Prospects for Therapy. Annu Rev Biochem. 77:701-26, 2008.*
Rich et al., Expression of cystic fibrosis transmembrane conductance regulator corrects defective chloride channel regulation in cystic fibrosis airway epithelial cells. Nature, 347(6291):358-63, 1990.*
Williams, Retriviral-fibronectin interactions in transduction of mammalian cells, Ann N Y Acad Sci., 872:109-13, 1999.*
Raju et al., Gain-of-function Chinese hamster ovary mutants LEC18 and LEC14 each express a novel N-acetylglucosaminyltransferase activity, J Biol Chem. 273(23):14090-8, 1998.*
Stanley, Biological consequences of overexpressing or eliminating N-acetylglucosaminyltransferase-TIII in the mouse, Biochim Biophys Acta. 1573(3):363-8, 2002.*
Moritz et al., Fibronectin improves transduction of reconstituting hematopoietic stem cells by retroviral vectors: evidence of direct viral binding to chymotryptic carboxy-terminal fragments, Blood 88(3):855-62, 1996.*
Asada et al. Enhancement of retroviral gene transduction on a dish coated with a cocktail of two different polypeptides: one exhibiting binding activity toward target cells, and the other toward retroviral vectors, J. Biochem. 123, 1041-1047, 1998.*
Rother et al, J Exp Med, 1995, 182:1345-1355.*
Tanemura et al, Biochem Biophys Res Commun, 1997, 235:359-364.*
Sensitivity to human serum of gammaretroviruses produced from pig endothelial cells transduced with glycosyltransferase genes, Miyazawa T. Kurihara et al, Xenotranplantation (2003) vol. 10, p. 562-568.
Vesicular stomatitis virus G glycoprotein pseudotyped retroviral vectors: Concentration to very high titer and efficient gene transfer into mammalian and nonmammalian cells, Jane C. Burns et al., Proc. Natl. Acad. Sci. USA (1993) vol. 90, p. 8033-8037.
Construction and Properties of Retrovirus Packaging Cells Based on Gibbon Ape Leukemia Virus, A. Dusty Miller et al., Journal of Virology (1991) vol. 65, No. 5 p. 2220-2224.

(Continued)

*Primary Examiner* — Marcia S Noble
*Assistant Examiner* — Chi-Feng Hsu
(74) *Attorney, Agent, or Firm* — Browdy and Neimark, PLLC

(57) ABSTRACT

The N-acetylglucosaminyltransferase III activity is enhanced in a cell carrying retrovirus-origin gag-pol gene and env gene. By constructing a retrovirus vector with the use of the above cell, a retrovirus vector having a modified sugar chain structure can be obtained. The retrovirus vector constructed by this method shows a high infection efficiency particularly in the presence of a functional substance.

8 Claims, 14 Drawing Sheets

(56) References Cited

OTHER PUBLICATIONS

Purification, cDNA Cloning, and Expression of UDP-N-acetylglucosamine: β-D-mannoside β-1,4N-Acetylglucosaminyltransferase III from Rat Kidney, A. Nishikawa et al., The Journal of Biological Chemistry (1992) vol. 267, No. 25, p. 18199-18204.

Chemical Modification of an Ecotropic Murine Leukemia Virus Results in Redirection of Its Target Cell Specificity, H. Neda et al., The Journal of Biological Chemistry (1991) vol. 266, No. 22, p. 14143-14146.

cDNA Cloning, Expression, and Chromosomal Localization of Human N-Acetylglucosamihnyltransferase III (GnT-III), Y. Ihara et al., J. Biochem. (1993) vol. 113, p. 692-698.

Colocalization of retrovirus and target cells on specific fibronectin fragments increases genetic transduction of mammalian cells, H. Hanenberg et al., Nature Medicine (1996) vol. 2, No. 8, p. 876-882.

A Safe Packaging Line for Gene Transfer: Separating Viral Genes on Two Different Plasmids, Dina Markowitz et al., Journal of Virology (1988) vol. 62, No. 4, p. 1120-1124.

Transfection of N-Acetylglucosaminyltransferase III Gene Suppresses Expression of Hepatitis B Virus in a Human Hepatoma Cell Line, HB611, E. Miyoshi et al., The Journal of Biological Chemistry (1995), vol. 270, No. 47, p. 28311-28315.

Merten, State-of-the-art of the production of retroviral vectors, The Journal of Gene Medicine, 6:S105-S124 (2004).

Donahue et al., Molecular Therapy, (2001), vol. 3, No. 3, pp. 359-367.

Korean Patent Office, Official Action, mailed Nov. 29, 2010 in Korean Patent Application No. 2007-7008675.

Japanese Patent Office, Office Action issued in Application No. 2006-537778, May 24, 2011.

\* cited by examiner

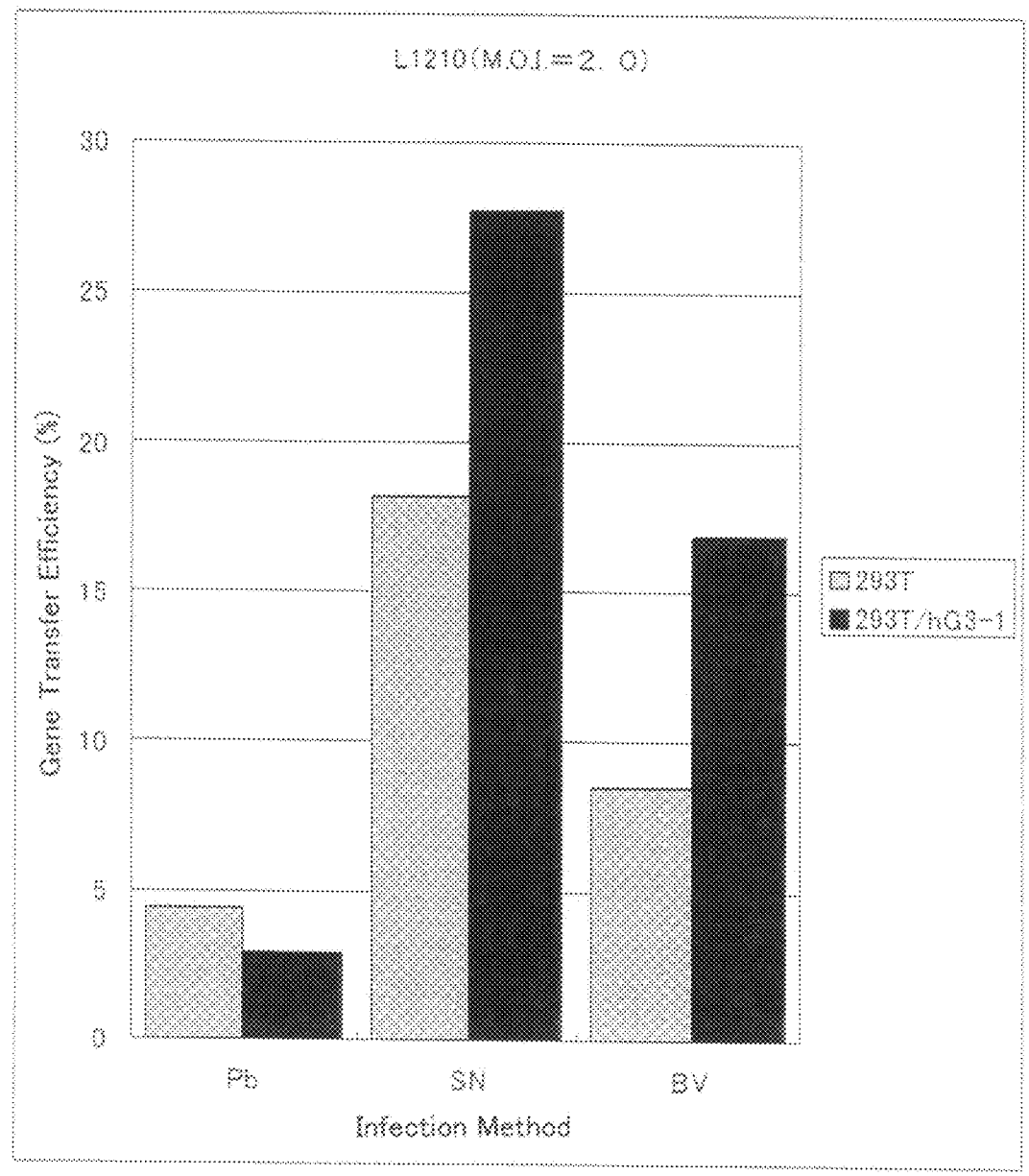

METHOD FOR PRODUCING RETROVIRUS USING HUMAN PRODUCER CELLS WITH INCREASED N-ACETYLGLUCOSAMINYLTRANSFERASE III ACTIVITY

TECHNICAL FIELD

The present invention relates to a retrovirus vector which is used for transferring a gene into a cell for transformation in fields of medicine, pharmacy, agriculture-forestry-fisheries and food science, a cell for producing the vector, and a method for transferring a gene into a cell using the vector.

BACKGROUND ART

Known methods for transferring a gene into a eukaryote include methods in which a virus vector is used, techniques in which a naked DNA is transferred by endocytosis, electroporation or a gene gun, and the like. The virus vectors are utilized in the filed of gene therapy for broad applications including basic and clinical ones. For example, adenovirus vectors are suitable for transient expression of a gene of interest in a target cell in large quantities. Retrovirus vectors can be used for long-term stable expression due to the function of stable integration into a host chromosome. It is expected that the vector can be used in the field of gene therapy of a genetic disease, or in the field of transgenic animal production. However, since the retrovirus vector results in gene transfer through viral infection, the tropism of the virus raises a problem. Gene transfer does not occur if the cell does not express a receptor on the cell surface. For overcoming this problem, efforts have been made to alter the host range by pseudotyping through modification of an envelope of a retrovirus vector, or to increase the titer. The pseudotyping of a retrovirus vector is mainly achieved by substituting an envelope protein derived from another virus species for an envelope protein in a conventional retrovirus vector (e.g., a vector derived from murine leukemia virus). For example, a retrovirus vector in which vesicular stomatitis virus envelope glycoprotein VSV-G is utilized to infect broad range of hosts (Patent Document 1, Non-patent Document 1), and a vector in which gibbon ape leukemia virus (GaLV) envelope is utilized to increase the efficiency of transfer into human hematopoietic stem cells (Patent Document 2, Non-patent Document 2) have been developed.

Aiming to modify only sugar chain modification of an envelope, which is a glycoprotein, without altering the amino acid sequence of the envelope protein, a technique in which $\alpha(1,3)$galactosyl epitope on the surface of a retrovirus is decreased for preventing inactivation of the retrovirus vector by humoral components has been examined (Patent Document 3). Disruption of a galactosyltransferase gene in a retrovirus producer cell, utilization of an inhibitor of sugar chain synthesis, utilization of a sugar chain-degrading enzyme and the like are proposed therein. However, gene disruption requires a complicated procedure, and it is necessary to determine suitable conditions for using the inhibitor of sugar chain synthesis or the sugar chain-degrading enzyme.

An N-acetylglucosaminyltransferase III (GnT-III) is an enzyme that transfers a bisecting N-acetylglucosamine (GlcNAc) residue to an N-linked sugar chain on a glycoprotein. GnT-III-encoding genes have been cloned from rat and human (Non-patent Document 3, Non-patent Document 4).

It has been reported that when a GnT-III gene is transferred into a cell infected with hepatitis B virus, production of the virus is inhibited because of suppression of viral gene expression (Non-patent Document 5). Regarding retroviruses, the influence of GnT-III on virus production or the infection efficiency of the produced virus is unknown.

Patent Document 1: WO 94/29440
Patent Document 2: WO 94/23048
Patent Document 3: WO 96/03520
Non-patent Document 1: J. C. Burns et al., Proc. Natl. Acad. Sci. USA, 90:8033-8037 (1993)
Non-patent Document 2: A. D. Miller et al., J. Virol. 65:2220-2224 (1991)
Non-patent Document 3: A. Nishikawa et al., J. Biol. Chem., 267:18199-18204 (1992)
Non-patent Document 4: Y. Ihara et al., J. Biochem., 113: 692-698 (1993)
Non-patent Document 5: E. Miyoshi et al., J. Biol. Chem., 270:28311-28315 (1995)

DISCLOSURE OF INVENTION

Problems to be Solved by the Invention

It is expected that pseudotyping through modification of an envelope of a retrovirus may be effective in altering the host range, increasing the infection efficiency or increasing the stability of virus particles. However, an envelope that can increase the infection efficiency cannot be readily obtained. Then, instead of modifying an envelope of a retrovirus, the present inventors modified a structure of a sugar chain on a cell membrane of a producer cell aiming to increase the infection efficiency of a virus.

Means to Solve the Problems

As a result of intensive studies, the present inventors have found the following. If a retrovirus vector is prepared using a cell in which an N-acetylglucosaminyltransferase III activity is enhanced and the retrovirus vector produced from the cell is used for gene transfer, the efficiency of gene transfer is significantly increased in the presence of a functional substance having a retrovirus-binding activity (e.g., a fibronectin fragment). Thus, the present invention has been completed.

The first aspect of the present invention relates to a cell having a gag-pol gene and an env gene derived from a retrovirus, in which an N-acetylglucosaminyltransferase III activity is enhanced.

The cell of the first aspect is exemplified by a cell in which the gag-pol gene and the env gene derived from the retrovirus are integrated into the chromosome, or a cell which is transformed with a plasmid containing the gag-pol gene and the env gene derived from the retrovirus.

According to the first aspect, an N-acetylglucosaminyltransferase III gene may be artificially transferred into the cell. For example, a cell in which the N-acetylglucosaminyltransferase III gene is integrated into the chromosome, or a cell which is transformed with a plasmid containing the gene may be used. The N-acetylglucosaminyltransferase III gene may be placed under the control of a heterologous promoter.

For example, the cell of the first aspect may be derived from a cell selected from the group consisting of 293 cell and 293T cell.

The second aspect of the present invention relates to a retrovirus producer cell, which is obtained by transforming the cell of the first aspect with a recombinant retrovirus vector.

The third aspect of the present invention relates to a method for producing a retrovirus vector comprising culturing the retrovirus producer cell of the second aspect; and collecting a culture supernatant.

The fourth aspect of the present invention relates to a retrovirus vector, which is produced according to the method for producing a retrovirus vector of the third aspect.

The fifth aspect of the present invention relates to a method for transferring a gene into a target cell comprising infecting a target cell with the retrovirus vector of the fourth aspect in the presence of a functional substance having a retrovirus-binding activity.

According to the fifth aspect, the functional substance having a retrovirus-binding activity is exemplified by fibronectin or a fragment thereof.

Effects of the Invention

The present invention provides a recombinant retrovirus vector which results in high gene transfer efficiency in the presence of a functional substance having a retrovirus-binding activity. By using the vector, a gene of interest can be stably transferred into a target cell with high efficiency. Since a retrovirus can be used for treatment of not only genetic diseases but also other various diseases, the present invention is widely useful in the field of medical treatment.

BRIEF DESCRIPTION OF DRAWINGS

FIG. 14 represents gene transfer efficiencies according to various infection methods using ecotropic retroviruses derived from 293T or a cell line 293T/hG3-1.

BEST MODE FOR CARRYING OUT THE INVENTION

Figure 1:
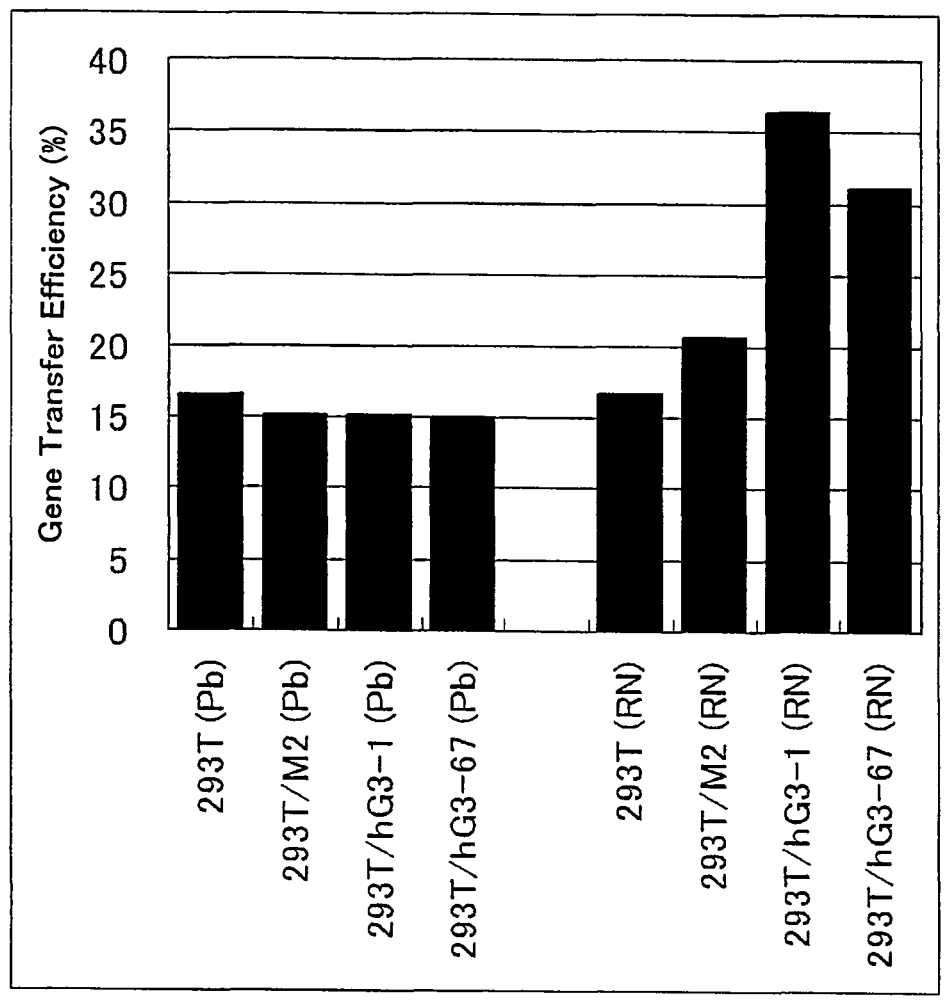
FIG. 1 represents gene transfer efficiencies observed using viruses derived from various clones.

A recombinant retrovirus vector is usually used according to the present invention. In particular, a replication-defective recombinant retrovirus vector is preferable. The replicability of such a vector is eliminated such that it cannot autonomously replicate in infected cells and, therefore, the vector is non-pathogenic. The vector can invade into a host cell such as a vertebrate cell (particularly, a mammalian cell) and stably integrate a foreign gene, which is inserted in the vector, into the chromosomal DNA.

There is no specific limitation concerning the foreign gene. Any gene of which the expression in the cell of interest is desired can be inserted. Examples thereof include genes encoding polypeptides (enzymes, growth factors, cytokines, receptors, structural proteins, etc.), antisense RNAs, ribozymes, decoys, and RNAs that cause RNA interference. According to the present invention, it is possible to use the foreign gene being inserted into a recombinant retrovirus vector such that the expression is controlled by an appropriate promoter (e.g., an LTR promoter in the retrovirus vector or a foreign promoter). Another regulatory element which cooperates with the promoter and with a transcription initiation site (e.g., an enhancer sequence) may be present in the vector in order to accomplish transcription of the foreign gene. Preferably, the transferred gene may contain a terminator sequence placed downstream. Furthermore, one may include an appropriate marker gene which enables selection of a cell having a transferred gene (e.g., a drug resistance gene, a gene encoding a fluorescent protein, a gene encoding an enzyme that can function as a reporter such as β-galactosidase or luciferase).

There is no specific limitation concerning the recombinant retrovirus vector used according to the present invention (also herein referred to as recombinant retrovirus). A known retrovirus vector such as a retrovirus vector (e.g., MFG vector, α-SGC vector (WO 92/07943), pBabe (Nucleic Acids Research, 18:3587-3596 (1990)), pLXIN (Clontech) or pDON-AI (Takara Bio)), a lentivirus vector (human immunodeficiency virus (HIV)-derived vector, simian immunodeficiency virus (SIV)-derived vector, etc.) or a modification thereof can be used.

The retrovirus vector of the present invention is a retrovirus vector that is subjected to sugar chain modification by the action of N-acetylglucosaminyltransferase III (hereinafter referred to as GnT-III). Modification of a sugar chain on the surface of a retrovirus particle takes place in a retrovirus producer cell. The retrovirus producer cell is produced by transforming a cell that has a gag-pol gene and an env gene derived from a retrovirus and in which an N-acetylglucosaminyltransferase III gene activity is enhanced with a retrovirus vector or a retrovirus vector plasmid corresponding to the vector.

General methods for producing a retrovirus vector include a method of production by transferring a recombinant retrovirus vector plasmid carrying a foreign gene and having a packaging signal into a retrovirus packaging cell into which a gag-pol gene and an env gene, which encode retroviral structural proteins, have been transferred; and a method of production by simultaneous transfection with an expression vector plasmid for a gag-pol gene and an env gene and a recombinant retrovirus vector plasmid carrying a foreign gene and having a packaging signal into a normal cell without a retroviral structural protein. Both methods can be used for the present invention.

According to the former one, if an efficient method is selected to transfect a recombinant retrovirus vector plasmid, it is possible to transiently produce a virus vector, or it is possible to establish a long-term stable expression cell line to obtain a retrovirus producer cell line. A known packaging cell line such as PG13 (ATCC CRL-10686), PA317 (ATCC CRL-9078), GP+E-86 or GP+envAM-12 (U.S. Pat. No. 5,278,056), or Psi-Crip (Proc. Natl. Acad. Sci. USA, 85:6460-6464 (1988)) can be used for this method.

Regarding the latter one, transient virus production is intended in most cases, and higher transfection efficiency is required for obtaining a high-titer virus. For example, 293 cell or 293T cell of which the transfection efficiency is high is used as a host in many cases.

For preventing appearance of a replication competent retrovirus particle, it is preferable that a gag-pol gene and an env gene are not located in proximity in a cell used according to the present invention. For example, it is preferable for the present invention to use a cell in which a gal-pol gene and an env gene are integrated at different positions on a chromosome, or a cell into which a plasmid containing a gag-pol gene and another plasmid containing an env gene are transferred.

The env gene is not limited to one encoding an envelope protein derived from the same virus as the retrovirus vector to be produced. A cell for pseudotyped packaging which has an env gene derived from a heterologous virus is also encompassed by the present invention. For example, an env gene derived from Moloney murine leukemia virus (MoMLV), gibbon ape leukemia virus (GaLV), vesicular stomatitis virus (VSV) or feline endogenous virus, or a gene encoding a protein that can function as env can be used as the env gene.

The present invention is not limited to a retrovirus vector producer cell. The cells of the present invention include a cell without a DNA having a packaging signal which is a genome of a recombinant retrovirus vector (transfer vector), provided that it can produce a retrovirus vector by transferring such a DNA.

By enhancing a GnT-III activity in a retrovirus producer cell, a retrovirus vector in which a sugar chain on a viral surface protein is modified is produced according to the present invention.

As used herein, enhancement of a GnT-III activity means that the GnT-III enzymatic activity in a cell is increased as compared with the normal level. Although it is not intended to limit the present invention, the GnT-III activity in the cell used as a retrovirus producer cell according to the present invention is five times or more higher, preferably ten times or more higher than the inherent GnT-III activity of the cell. Increase in a GnT-III enzymatic activity can be confirmed, for example, by measuring a GnT-III activity or by measuring an amount of mRNA transcribed from a GnT-III-encoding gene using a known method (e.g., RT-PCR or Northern hybridization).

Enhancement of a GnT-III activity can be accomplished by a known procedure such as expression induction of a GnT-III-encoding gene on a chromosome, modification of a GnT-III gene on a chromosome (increase in copy number, insertion of a promoter, an enhancer or the like), transfer of a GnT-III gene into a cell, or obtainment of a GnT-III gene high expression cell line by mutagenesis of a cell.

The structure of the gene encoding human GnT-III is known (J. Biochem., 113:692-698 (1993)). It is possible to modify a GnT-III gene on a chromosome on the basis of this information. For example, the position of a GnT-III-encoding gene in the cell to be used as a retrovirus producer cell is determined; a heterologous promoter which is different from the one naturally located upstream of the gene and controlling the expression of the gene (e.g., a strong promoter or an inducible promoter) is inserted into a region upstream of the gene; and it is then possible to increase the expression level of the gene. It is possible to obtain a cell in which a GnT-III activity is enhanced more readily according to the method for artificially transferring a GnT-III-encoding gene into a cell as described in Examples.

A GnT-III-encoding gene can be transferred into a cell by transferring the gene being inserted in a vector into a host. An appropriate vector may be selected from known ones. For example, a plasmid vector, a virus vector or the like may be used. If a plasmid vector is to be used, it can be transferred into a cell, for example, using a conventional transfection method (a calcium phosphate method, a cationic liposome method, etc.). Furthermore, a procedure by which a transferred GnT-III-encoding gene is integrated into a chromosomal DNA in a cell may be used. According to the present invention, expression of a GnT-III in a retrovirus producer cell may be transient expression or stable expression.

A membrane localization signal is present at the N terminus of a retrovirus envelope protein. It is considered as follows: a sugar chain is attached to the envelope protein in a cell; the protein is cleaved by a proteolytic enzyme into a TM protein and a SU protein; and a multimer is formed and expressed on the cell membrane surface. A gag-pol fusion protein and a gag protein form a capsid just beneath the cell membrane, and a genomic RNA is incorporated to complete assembly, leading to budding from the cell. The retrovirus buds being wrapped by a lipid bilayer of the host cell. It is expected that a surface protein on a virus particle of a retrovirus produced from a cell highly expressing a glycosyltransferase is subjected to sugar chain modification. Thus, although it is not intended to limit the present invention, it is considered as follows. If a GnT-III activity is enhanced in a virus producer cell, a sugar chain having the bisecting GlcNAc structure of Chemical Formula 1 below is attached to a membrane protein derived from the cell or a virus envelope protein. The sugar chain is generated by the action of GnT-III. Alternatively, the ratio of an oligomannose type or hybrid type sugar chain modification may be increased.

[Chemical Formula 1]

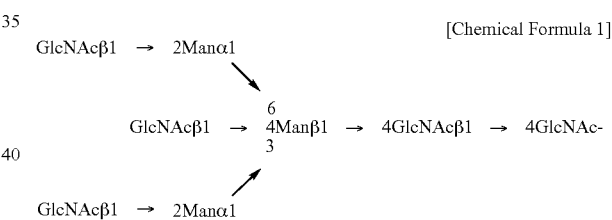

For example, a retrovirus having a sugar chain modified with GnT-III can be obtained from a culture supernatant of a cell line stably expressing GnT-III, which is obtained by transferring a GnT-III expression vector plasmid into a retrovirus producer cell. It is also possible to obtain a GnT-III-modified retrovirus as follows: a GnT-III expression vector plasmid is transferred into 293 cell, 293T cell or the like to obtain a cell line stably expressing GnT-III; and 293 cell, 293T cell or the like having the transferred GnT-III is transfected simultaneously with an expression vector plasmid for gag-pol and env genes, and a recombinant retrovirus vector plasmid carrying a foreign gene and having a packaging signal. Alternatively, it is possible to obtain a GnT-III-modified retrovirus by transfecting 293 cell, 293T cell or the like simultaneously with a GnT-III expression vector plasmid, an expression vector plasmid for gag-pol and env genes, and a recombinant retrovirus vector plasmid carrying a foreign gene and having a packaging signal. The thus obtained retrovirus vector can be filtered through a 0.45-μm filter and stored in a deep freezer until use.

A recombinant retrovirus prepared from a cell in which a GnT-III activity is enhanced according to the method of the present invention results in excellent infection efficiency particularly in gene transfer in the presence of a functional substance having a retrovirus-binding activity.

Gene transfer methods in which a functional substance having a retrovirus-binding activity is used are described, for example, in WO 95/26200, WO 97/18318, or Nature Medicine, 2:876-882 (1996). Such methods include a method in which a functional substance having both a retrovirus-binding site and a target cell-binding site in the same molecule is used, and a method in which a mixture of a functional substance having a retrovirus-binding site and a functional substance having a target cell-binding site is used. The retrovirus prepared according to the method of the present invention can be used for both of the methods.

There is no specific limitation concerning the functional substance as long as it has a retrovirus-binding activity and/or a target cell-binding activity. Examples of functional substances having a retrovirus-binding activity include a heparin-binding domain from fibronectin (heparin-II domain), fibroblast growth factor, type V collagen fragments, derivatives and variants of the above-mentioned polypeptides, polylysine and DEAE-dextran. Any substance capable of binding to a target cell of interest can be used as a functional substance having a target cell-binding activity. Although it is not intended to limit the present invention, examples of functional substances having a target cell-binding activity include polypeptides having a cell-binding activity (cytoskeletal proteins, etc.), antibodies that recognize a cell or a biomolecule on a cell surface, growth factors, cytokines and sugar chains.

In one embodiment of the method for transferring a gene into a target cell according to the present invention, a target cell is infected, in the presence of a functional substance containing a heparin-binding domain from fibronectin, with a recombinant retrovirus prepared from a cell in which a GnT-III activity is enhanced. A preferable exemplary functional substance is a fibronectin fragment having both a cell adhesion domain and a heparin-binding domain. A cell adhesion domain that binds to VLA-5 and/or VLA-4 is particularly preferable as the cell adhesion domain. Such a fibronectin fragment can be prepared from fibronectin purified from a living body using a means such as digestion with a protease, or it can be produced using recombinant DNA techniques. For example, a recombinant fibronectin fragment sold by Takara Bio under the name of RetroNectin, which has a heparin-binding domain, a VLA-5-binding domain and a VLA-4-binding domain, is preferable for the present invention.

EXAMPLES

The following Examples illustrate the present invention in more detail, but are not to be construed to limit the scope thereof.

Example 1

Construction of Plasmid Vector for Expressing Human GnT-III

A DNA fragment containing a DNA encoding human GnT-III (GenBank E13194, SEQ ID NO:1) was prepared and inserted between NcoI and Sse8387I sites in a plasmid vector for gene expression pTriEx-3 Hygro (Novagen) to construct a recombinant plasmid. This recombinant plasmid is designated as phG3-Hygro.

This plasmid was used to transform *Escherichia coli* JM109, and one transformant colony was cultured with shaking in 5 ml of LB medium at 37° C. for 8 hours. Then, it was subjected to expanded cultivation in 80 ml of LB medium, and the plasmid DNA was purified using QIA filter Plasmid Maxi Kit (Qiagen).

Example 2

1. Isolation of 293T Cell Transfer Clone

Human 293T cells (Mol. Cell. Biol., 7:379-387 (1987)) were cultured using Dulbecco's modified Eagle medium (DMEM, Sigma) containing 10% fetal calf serum (JRH) as a growth medium at 37° C. with 5% $CO_2$. $3\times10^6$ human 293T cells were seeded into each 6-cm tissue culture plate (Iwaki Glass) and cultured overnight. On the next day, it was confirmed that human 293T cells reached semi-confluence, the medium was removed by suction, and 3 ml of the fresh growth medium was added to each plate.

10 μg of phG3-Hygro and 62 μl of 2 M $CaCl_2$ were mixed with sterile distilled water up to 500 μl in a polystyrene round-bottom tube (Falcon). Immediately after adding 500 μl of transfection buffer (50 mM HEPES, 10 mM KCl, 12 mM D-glucose, 280 mM NaCl, 1.5 mM $Na_2HPO_4$ (pH 7.10)), the mixture was subjected to bubbling for 20 seconds utilizing excretion from an electric pipetter. The prepared solution was homogeneously added dropwise to the above-mentioned plate containing 293T cells. 293T cell having pTriEx-3 Hygro (mock) transferred in a similar manner was prepared as a control. These cells were cultured at 37° C. with 5% $CO_2$ for 9 hours. Then, the culture supernatant was removed by suction, 4 ml of a fresh growth medium was added to each plate, and the cells were cultured at 37° C. with 5% $CO_2$. Each of the human 293T cells was detached from the plates by treatment with trypsin (Gibco) two days after the transfection, and suspended in 10 ml of the growth medium. The cell number was counted, and the cells were seeded into each 10-cm tissue culture plate (Iwaki Glass) at a density of $6\times10^6$, $4\times10^6$ or $2\times10^6$ cells/plate, and cultured at 37° C. with 5% $CO_2$. A growth medium containing hygromycin (Invitrogen) at a concentration of 0.3 mg/ml was used for cultivation from the next day.

After culturing for 16 days with the hygromycin-selection medium while exchanging the medium every three or four days, the appeared hygromycin-resistant colonies were cloned using cloning rings (Iwaki Glass), and seeded into wells of a 48-well tissue culture plate (Iwaki Glass). The respective cloned human 293T cells were cultured while passaging using 24-well tissue culture plates (Iwaki Glass), 6-cm plates and 10-cm plates according to the growth rates. Finally, the following were obtained: 10 mock-transferred human 293T cell clones into which pTriEx-3 Hygro was transferred as a control (293T/M); and 20 human 293T cell clones into which phG3-Hygro was transferred (293T/hG3).

2. Confirmation of Expression

Total RNA was extracted from $1\times10^7$ cells of each 293T/hG3 clone obtained in "1" above using TRIzol (Invitrogen). A cDNA was synthesized using the total RNA as a template as follows. A reaction mixture was prepared by mixing 1 μl of AMV Reverse Transcriptase XL (5 U/μl, Life Sciences), 2 μl of 10×RNA PCR buffer (Takara Bio), 0.5 μl of RNase Inhibitor (40 U/μl), 1 μl of Random 9mers (50 pmol/μl), 2 μl of dNTP mix (10 mM each), 4 μl of 25 mM $MgCl_2$, 1 μl of the template (corresponding to 1 μg) and RNase-free distilled water to a total volume of 20 μl. The reaction mixture was reacted as follows: 30° C. for 10 minutes; 42° C. for 30 minutes; 99° C. for 5 minutes; and 4° C. for 5 minutes. After reaction, detection of human GnT-III gene was carried out by a PCR reaction using 1 μl of the reaction mixture as a template and a pair of human GnT-III-specific primers (hG3-F1 (SEQ ID NO:2) and hG3-R4 (SEQ ID NO:3)). The reaction was carried out as follows: 94° C. for 5 minutes; 30 cycles of 94° C. for 30 seconds, 56° C. for 30 seconds and 72° C. for 30 seconds; and finally 72° C. for 7 minutes. phG3-Hygro was used as a positive control, and 1 μl of an RT-PCR product prepared from a 293T/M clone in a similar manner was used as a negative control. After PCR reaction, 8 μl each of the reaction mixtures was subjected to electrophoresis on 2% agarose gel to observe amplified fragments. As a result, although amplification of a fragment from human GnT-III gene was observed even for the negative control, the amounts of the amplification products obtained using the templates prepared from the 293T/hG3 clones were increased as compared with the negative control. Thus, it was shown that human GnT-III derived from phG3-Hygro was expressed in the 293T/hG3 clones isolated in "1" above.

3. Quantification of GnT-III Enzymatic Activity $10^6$ to $10^7$ cells of each of two 293T/hG3 clones (cell lines 293T/hG3-1 and 293T/hG3-67) and two 293T/M clones (cell lines 293T/M2 and 293T/M3) obtained in "1" above as well as 293T cell were collected, and washed with PBS. 100 μl of Cellytic™ M Cell Lysis Reagent (Sigma) was added to a precipitate obtained by centrifugation, and mixed at room temperature for 15 minutes. After centrifugation at 20400×g for 15 minutes, a supernatant was collected as a GnT-III crude enzyme solution and subjected to activity measurement. A portion of the crude enzyme solution was subjected to protein quantification using BCA Protein Assay Reagent kit (Pierce).

A mixture of 3 μl of a GnT-III crude enzyme solution, 5 μl of 2× buffer (250 mM MES-NaOH (pH 6.25), 200 mM $MnCl_2$, 400 mM N-acetylglucosamine (GlcNAc), 1.0% Triton X-100), 1 μl of 0.2 M UDP-GlcNAc and 1 μl of Gn,Gn-bi-PA (385 pmol/μl, Takara Bio, PA-Sugar Chain O12, the structure is shown in Chemical Formula 2 below) was reacted at 37° C. for 2 hours. After reaction, 10 μl of a reaction termination solution (2% sodium tetraborate, 250 mM EDTA) was added thereto, the enzyme was inactivated by heating at 98° C. for 5 minutes, and a supernatant was obtained by centrifugation at 20400×g for 3 minutes. 10 μl of the supernatant was analyzed using HPLC as follows: column: PALPAK Type R (CA8000: 4.6 mm φ×250 mm, Takara Bio); eluent: 100 mM triethylamine acetate buffer (pH 4.0) containing 0.5% 1-butanol; column temperature: 40° C.; and flow rate: 1.0 ml/minute. A fluorescence detector was used for detection with an excitation wavelength of 320 nm and an emission wavelength of 400 nm. Under these conditions, a sugar chain Gn,Gn-bi-PA was eluted at 9.6 minutes and a sugar chain Gn(Gn)Gn-bi-PA was eluted at 18.1 minutes. The GnT-III activity was judged as a specific activity of GnT-III calculated based on the amount of generated Gn(Gn)Gn-bi-PA (the structure is shown in Chemical Formula 3 below) and the previously determined protein amount of the crude enzyme solution. As a result, the GnT-III activities were as follows defining the activity for 293T cell as 1.0: the cell line 293T/M2: 2.4; the cell line 293T/M3: 1.0; the cell line 293T/hG3-1: 32.2; and the cell line 293T/hG3-67: 59.3. Based on the above, it was shown that the GnT-III enzymatic activities were enhanced in 293T/hG3 clones due to human GnT-III gene derived from phG3-Hygro.

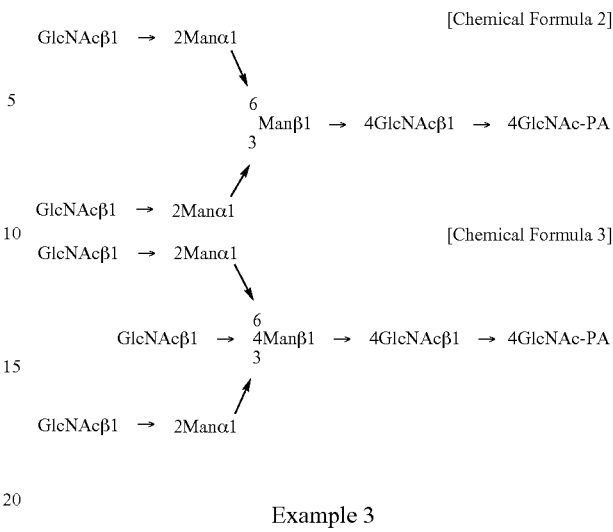

Example 3

Preparation of Virus from 293T/hG3 Clone

1. Preparation of Virus Supernatant

Among the 293T/hG3 clones isolated in Example 2 above, seven clones for which expression of GnT-III gene was confirmed were selected, and amphotropic retrovirus supernatants were prepared from them. The same procedures were conducted using 293T cell and two 293T/M clones in control experiments. $1.5 \times 10^6$ cells of each cell clone were seeded into each well of a 6-well tissue culture plate (Iwaki Glass), and cultured overnight in 2 ml of DMEM containing 10% fetal calf serum at 37° C. with 5% $CO_2$. On the next day, it was confirmed that each cell clone reached semi-confluence, the medium was removed by suction from each well, and 1.5 ml of fresh DMEM containing 10% fetal calf serum was added to each well. Chloroquin (Wako Pure Chemical Industries) at a final concentration of 25 μM was further added to each well. The followings were combined in a polystyrene round-bottom tube: 27.5 μg of a plasmid vector pGP (Takara Bio) for expressing retrovirus structural protein gag-pol; 27.5 μg of a plasmid vector pE-ampho (Takara Bio) for expressing amphotropic env; 55 μg of a plasmid vector for retrovirus production in which a gene for a jellyfish-derived red-shift green fluorescent protein (rsGFP) in a plasmid pQBI25 (Quantum Biotechnologies) is inserted into a retrovirus vector plasmid pDON-AI (Takara Bio); 341 μl of 2 M $CaCl_2$; and sterile distilled water to 2750 μl. The mixture was divided into two 1300-μl portions. Immediately after adding 1300 μl of transfection buffer to each tube, the mixture was subjected to bubbling for 20 seconds utilizing excretion from an electric pipetter. 500 μl of the mixture was homogeneously added dropwise to each well. The plate was incubated at 37° C. with 5% $CO_2$ for 9 hours. Then, 1.5 ml of the culture supernatant was removed, 2 ml of fresh DMEM containing 10% fetal calf serum was added to each well, and the cultivation was continued. The medium in each well was exchanged for 2 ml of fresh DMEM containing 10% fetal calf serum 24 hours after the gene transfer. After further culturing for 24 hours, the culture supernatant was collected, filtered through a 0.45-μm filter (Millipore), and stored as a virus supernatant stock at −80° C. until use.

2. Measurement of Titer of Virus Supernatant

A titer of a virus supernatant was measured using NIH/3T3 cells (ATCC CRL-1658) according to a standard method (J.

Virol., 62:1120-1124 (1988)). Specifically, $5 \times 10^4$ NIH/3T3 cells in 2 ml of DMEM containing 10% bovine serum (Gibco) were added to each well of a 6-well tissue culture plate, and cultured overnight at 37° C. with 5% $CO_2$. The medium was removed by suction, 1 ml of a serial dilution of the virus supernatant was added to the well, and hexadimethrine bromide (polybrene, Aldrich) at a final concentration of 8 μg/ml was further added thereto. The cells were cultured at 37° C. with 5% $CO_2$ for 4 to 6 hours. 1 ml of DMEM containing 10% bovine serum was further added thereto, and the cultivation was continued for 72 hours. The cells collected from the plate were subjected to analysis using a flow cytometer FACS Vantage (Becton-Dickinson), and the ratio of NIH/3T3 cells expressing rsGFP was determined. The number of infectious particles in 1 ml of a supernatant (I.V.P./ml) was calculated based on a value obtained by multiplying the number of input cells per well by the ratio of rsGFP-expressing cells and the dilution rate of the virus supernatant to determine the virus titer. The viruses were prepared several times for measuring the virus titers. The titers of virus supernatants derived from the 293T/hG3 clones ranged from $1.9 \times 10^5$ I.V.P./ml to $2.8 \times 10^6$ I.V.P./ml. The titer of virus supernatant derived from 293T cell used in a control experiment ranged from $9.4 \times 10^5$ I.V.P./ml to $1.6 \times 10^6$ I.V.P./ml, and the titers of virus supernatants derived from the 293T/M clones used in control experiments ranged from $1.8 \times 10^6$ I.V.P./ml to $2.6 \times 10^6$ I.V.P./ml.

Example 4

1. Preparation of CH-296-Coated Plate

500 μl of fibronectin fragment CH-296 (RetroNectin, Takara Bio) at a concentration of 32 μg/ml was added to each well of a 24-well non-tissue culture treated plate (Falcon). The plate was allowed to stand at 4° C. overnight, subjected to blocking with 2% BSA/PBS at room temperature for 30 minutes, and washed with PBS. This plate was used as a CH-296-coated plate and prepared when necessary.

2. Gene Transfer into NIH/3T3 Cell

Among the virus supernatants prepared in Example 3, viruses prepared from the cell lines 293T/hG3-1 and 293T/hG3-67 as human GnT-III-modified viruses were selected for use in gene transfer into NIH/3T3 cells. A virus prepared from 293T cell was used as a control, and a virus prepared from the cell line 293T/M2 was selected as a mock virus. These viruses were used to infect NIH/3T3 cells in the CH-296-coated plate, and the change in infectivity was examined for a retrovirus prepared from a cell having transferred human GnT-III gene as follows.

NIH/3T3 cells grown to semi-confluence in a 10-cm plate were detached from the plate by treatment with trypsin, suspended in 10 ml of DMEM containing 10% bovine serum, and collected by centrifugation at 190×g for 3 minutes. The viable-cell number was counted, and the cell density was adjusted to $2 \times 10^5$ cells/ml in DMEM containing 10% bovine serum. The respective virus supernatants obtained in Example 3 were adjusted to $2 \times 10^4$ I.V.P./ml by dilution with DMEM containing 10% fetal calf serum (JRH) 100 μl of the NIH/3T3 cell suspension, 200 μl of the diluted virus supernatant and 200 μl of DMEM containing 10% bovine serum were added to each well of a CH-296-coated plate. The cells were cultured for three days at 37° C. with 5% $CO_2$. After three days, NIH/3T3 cells were subjected to analysis using a flow cytometer FACS Vantage, and the ratio of NIH/3T3 cells expressing rsGFP was determined as the gene transfer efficiency. In a control experiment for the infection using a CH-296-coated plate, $2 \times 10^4$ NIH/3T3 cells in 500 μl of DMEM containing 10% bovine serum were added to each well of a 24-well tissue culture plate. After culturing overnight at 37° C. with 5% $CO_2$, the medium was removed by suction, 200 μl of the virus supernatant at $2 \times 10^4$ I.V.P./ml prepared as described above and 300 μl of DMEM containing 10% bovine serum were added to each well. Polybrene was further added at a final concentration of 8 μg/ml. The cells were cultured for three days at 37° C. with 5% $CO_2$. After three days, NIH/3T3 cells were subjected to a flow cytometer FACS Vantage to determine the ratio of NIH/3T3 cells expressing rsGFP.

The results of the above-mentioned experiments are shown in FIG. 1. In the figure, the cells from which the virus supernatants were prepared are indicated along the horizontal axis. (Pb) represents the group of infection in the presence of polybrene, and (RN) represents the group of infection using the CH-296-coated plate. The longitudinal axis represents the gene transfer efficiency (%).

As to the control experiments in which infection was carried out using polybrene, the ratios of NIH/3T3 cells expressing rsGFP for the respective viruses were almost equivalent to each other. When the CH-296-coated plate was used, the ratio of rsGFP-expressing cells for NIH/3T3 cells infected with the human GnT-III-modified virus was increased by 1.7- to 2.2-fold as compared with the ratio for NIH/3T3 cells infected with the unmodified virus (FIG. 1). This shows that the infectivity of a retrovirus of which the membrane surface is modified with human GnT-III is increased when a CH-296-coated plate is used.

3. Gene Transfer into Hemocytic Cell

Figure 2:
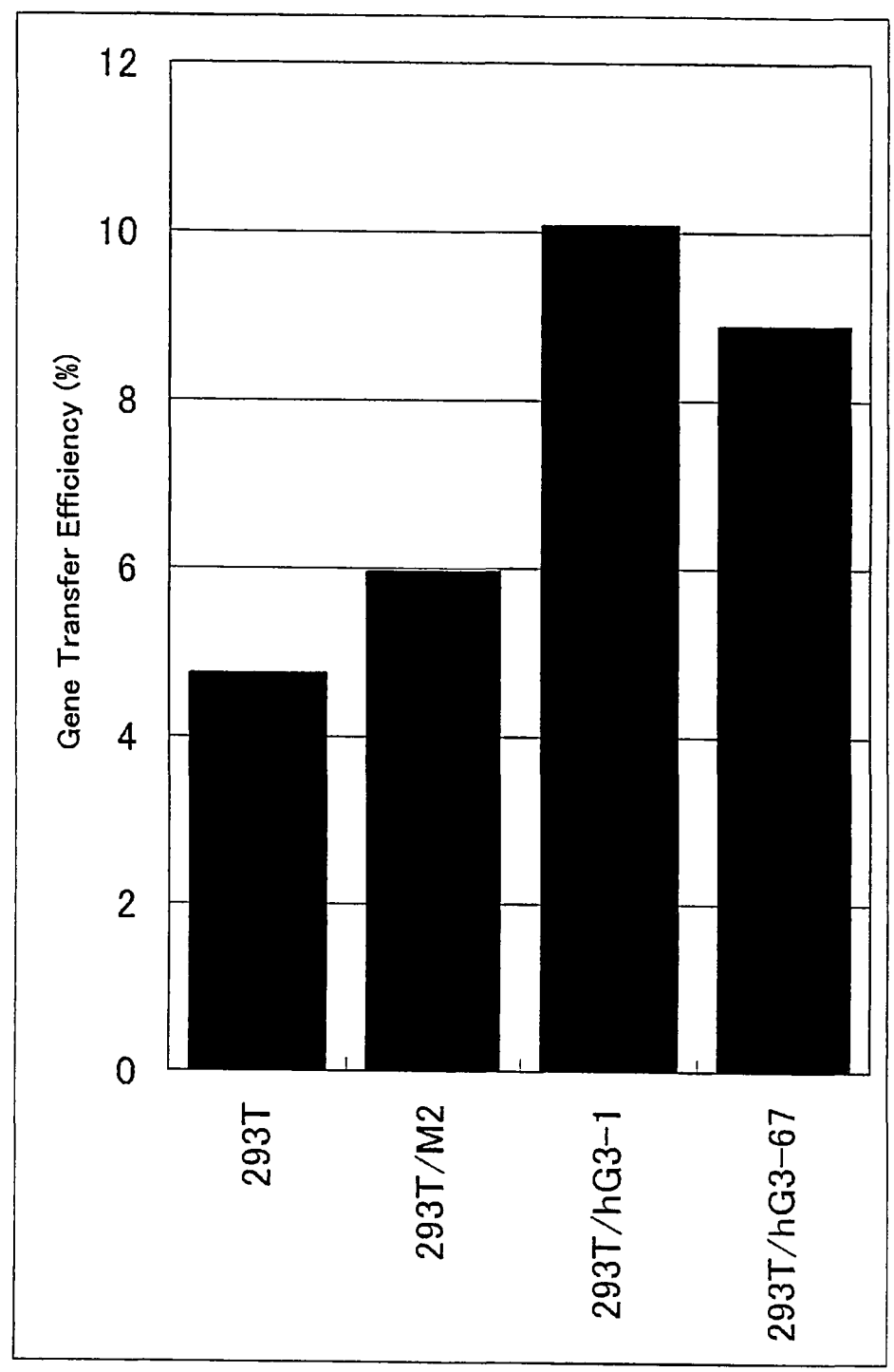
FIG. 2 represents gene transfer efficiencies observed using viruses derived from various clones.
Figure 3:
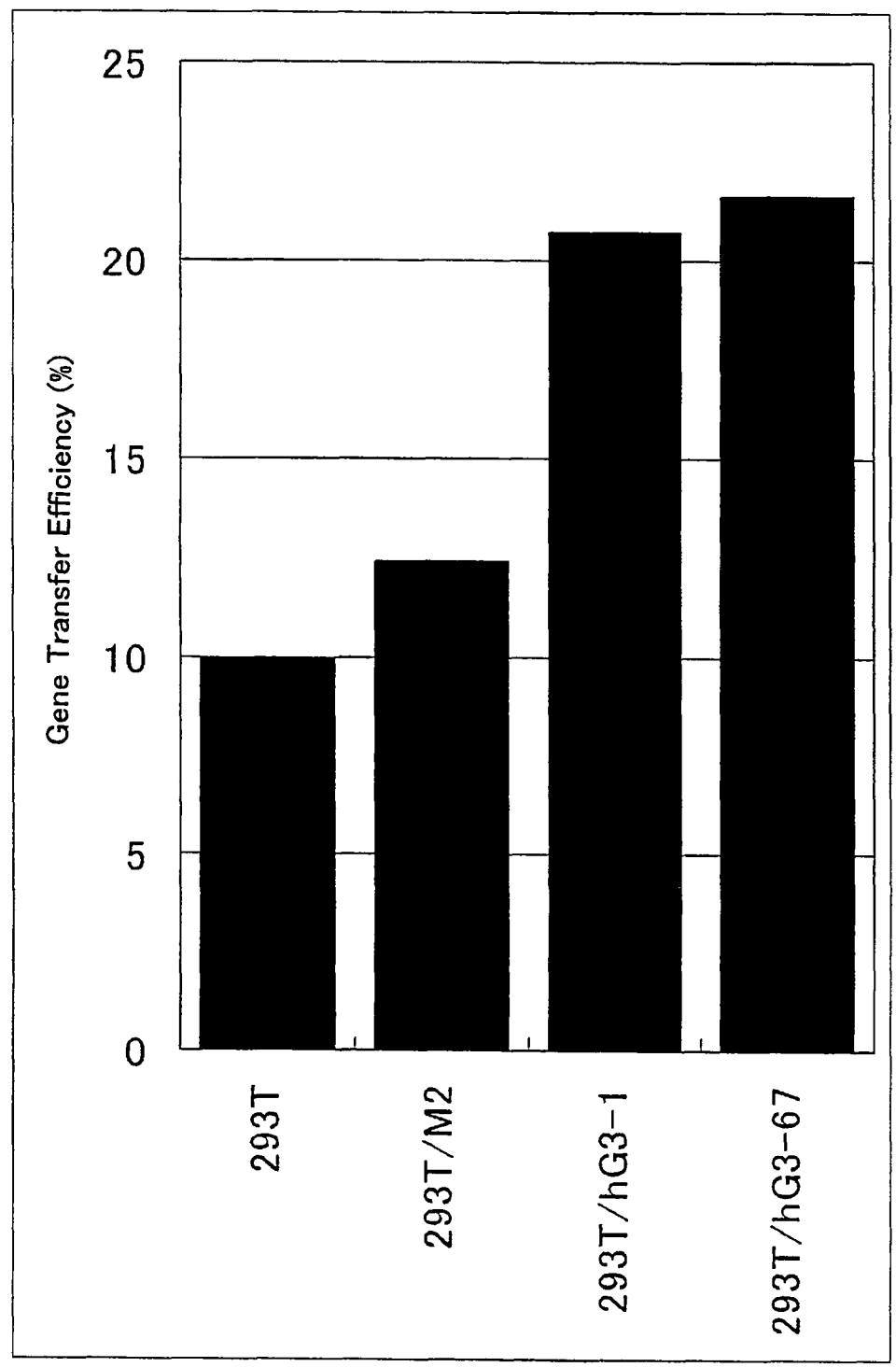
FIG. 3 represents gene transfer efficiencies observed using viruses derived from various clones.
Figure 4:
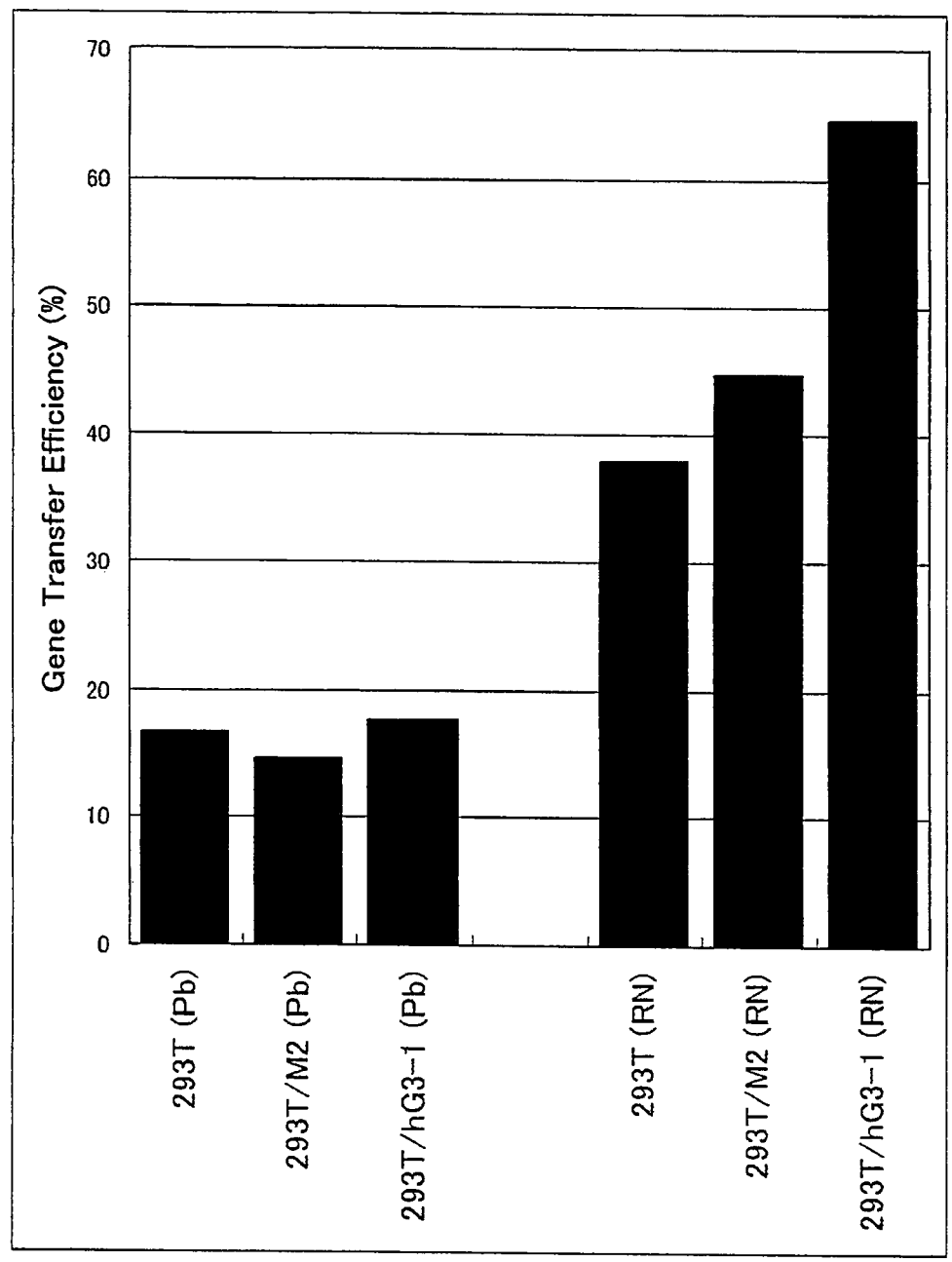
FIG. 4 represents gene transfer efficiencies observed using viruses derived from various clones.
Figure 5:
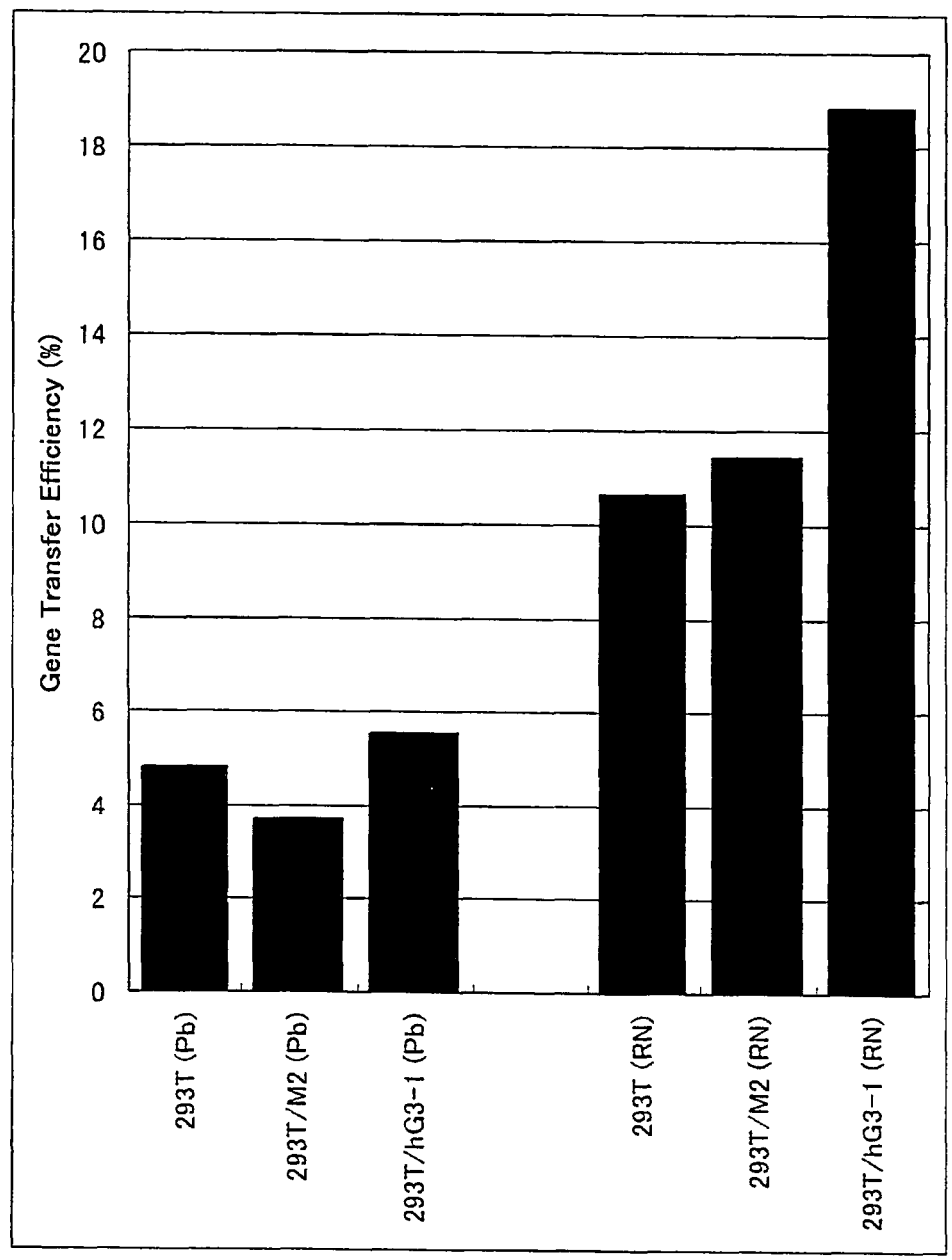
FIG. 5 represents gene transfer efficiencies observed using viruses derived from various clones.
Figure 6:
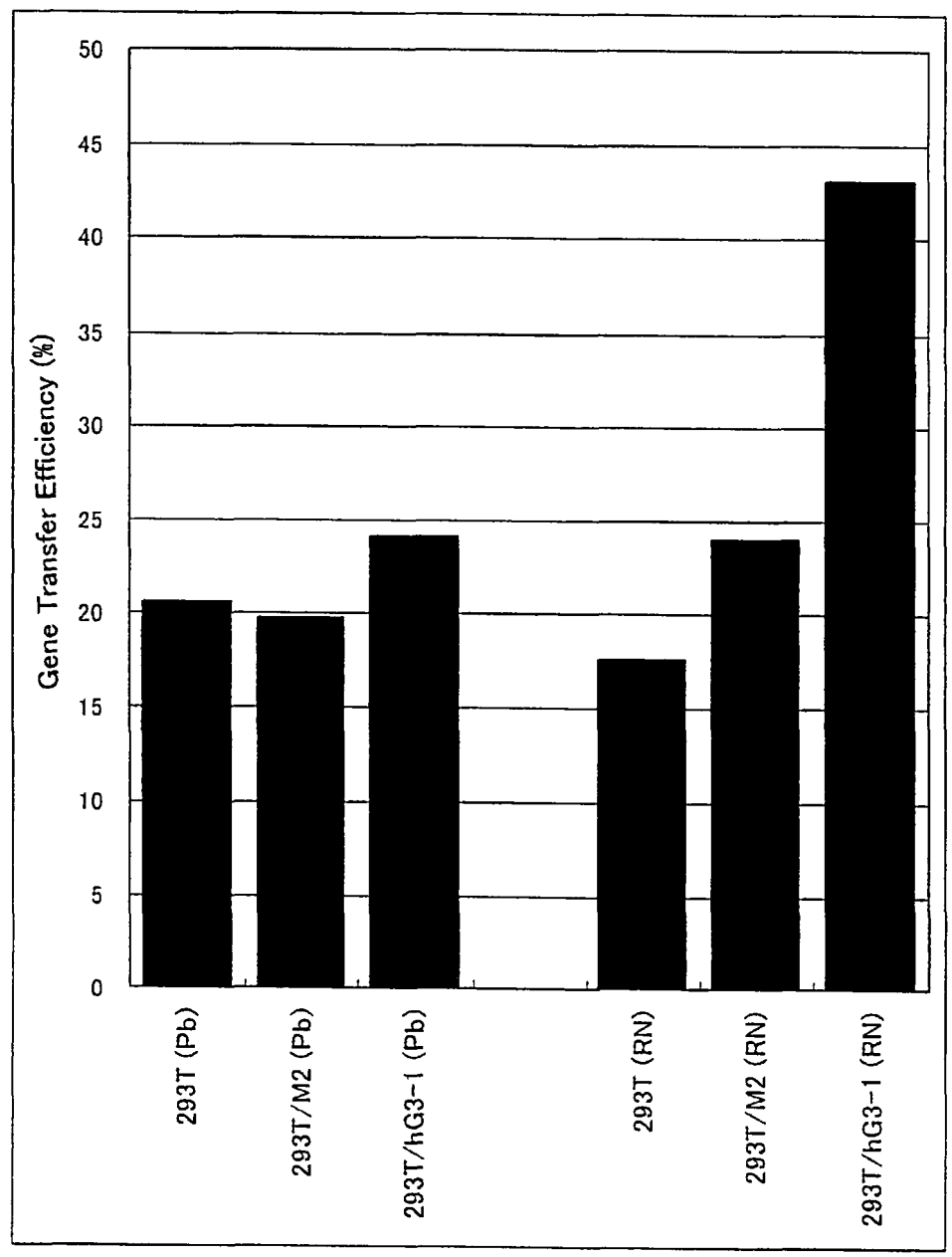
FIG. 6 represents gene transfer efficiencies observed using viruses derived from various clones.
Figure 7:
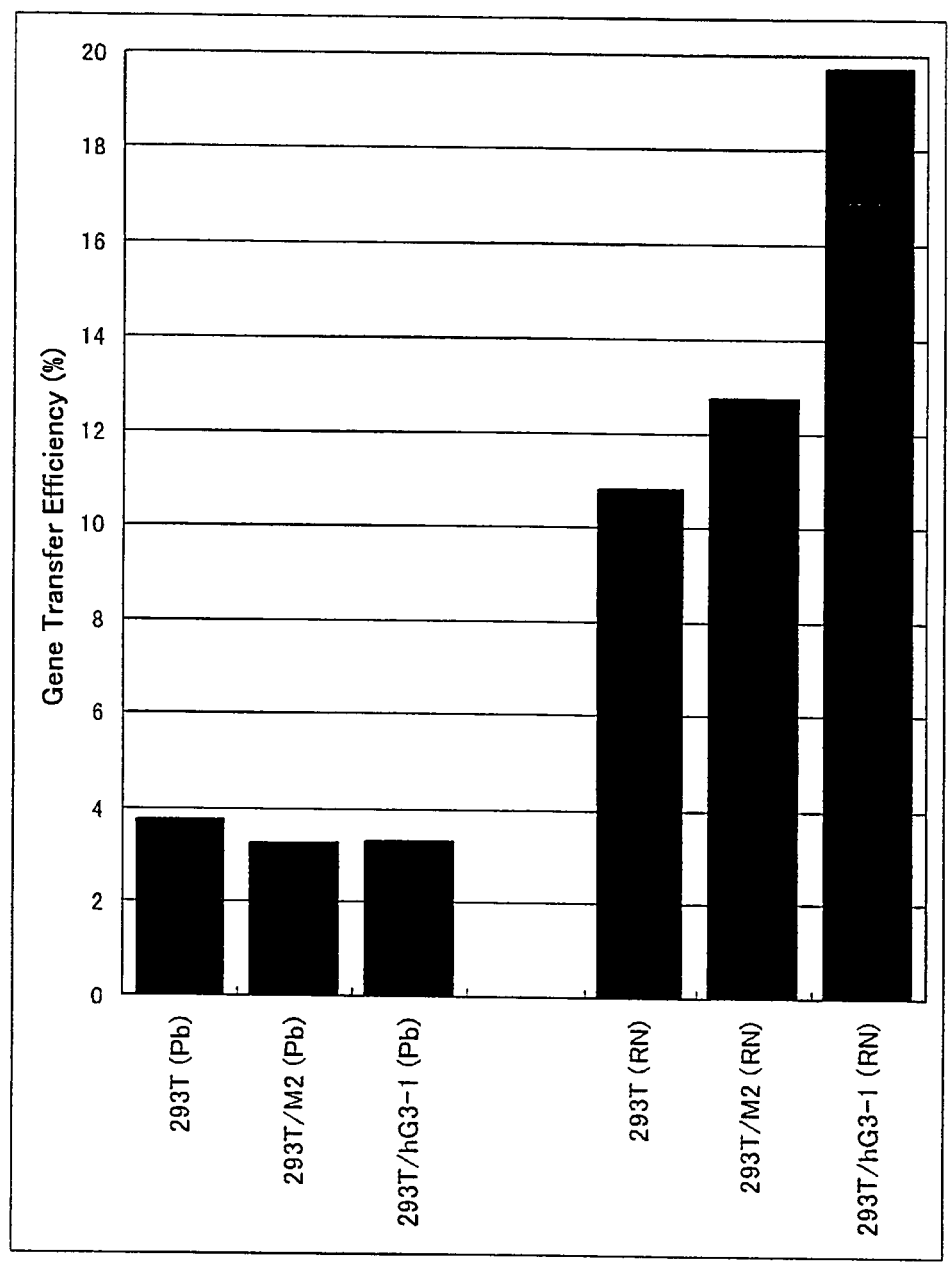
FIG. 7 represents gene transfer efficiencies observed using viruses derived from various clones.
Figure 8:
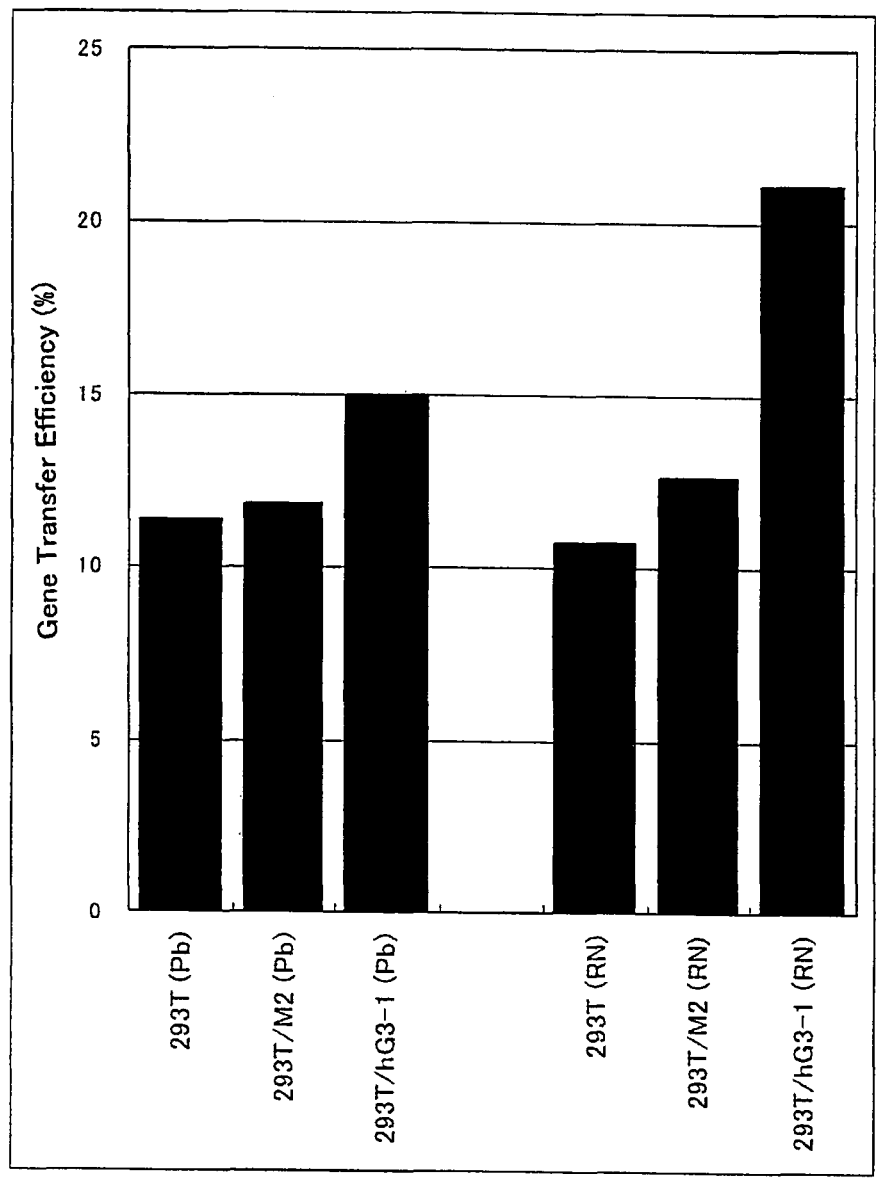
FIG. 8 represents gene transfer efficiencies observed using viruses derived from various clones.
Figure 9:
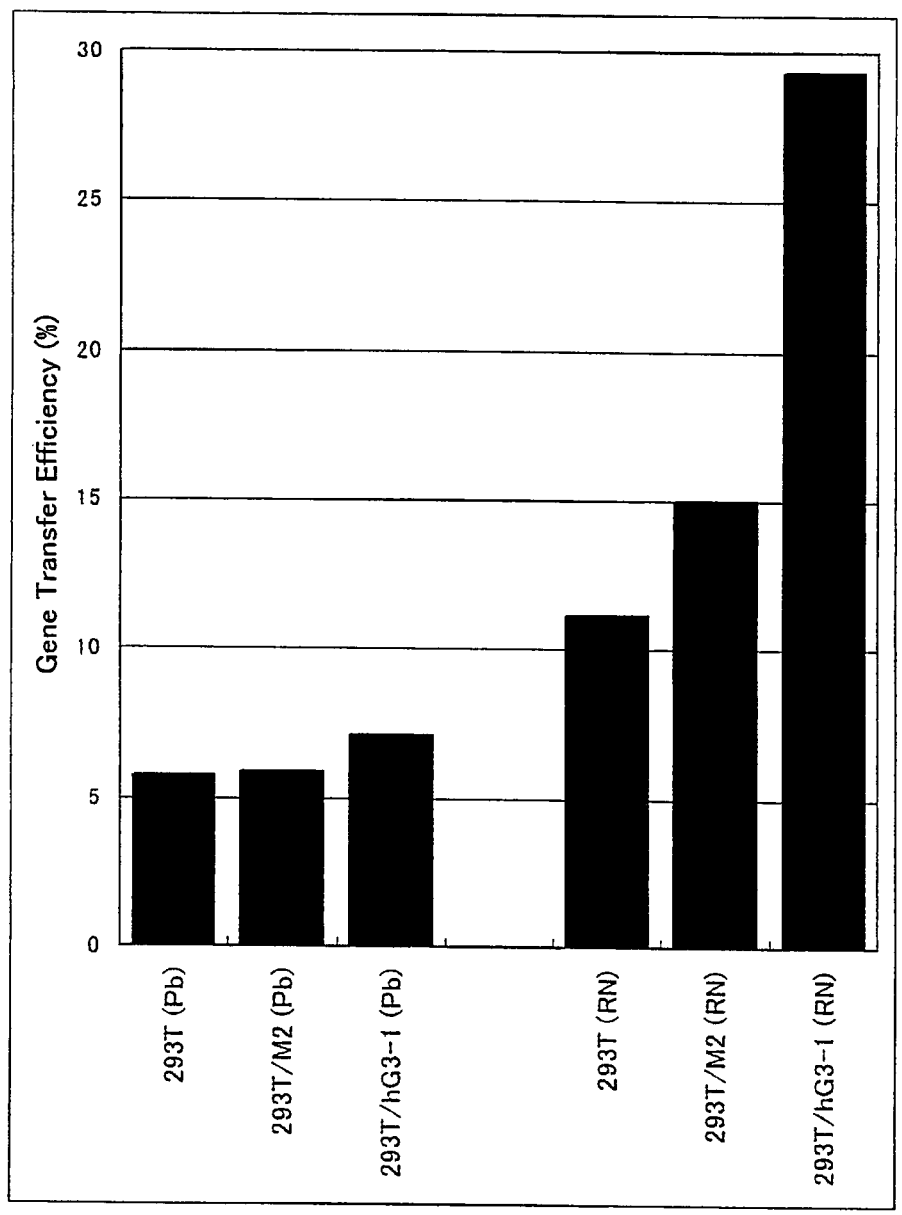
FIG. 9 represents gene transfer efficiencies observed using viruses derived from various clones.

Human K562 cells (ATCC CCL-243) were cultured using RPMI-1640 (Sigma) containing 10% fetal calf serum as a growth medium at 37° C. with 5% $CO_2$. Human TF-1 cells (ATCC CRL-2003) were cultured using RPMI-1640 containing 10% fetal calf serum as a growth medium in the presence of granulocyte-macrophage colony-stimulating factor (GM-CSF, Schering-Plough) at a final concentration of 2 ng/ml at 37° C. with 5% $CO_2$. The virus supernatant prepared in Example 3 was subjected to infection according to the method as described in "2" above using a CH-296-coated plate at M.O.I. (multiplicity of infection)=0.2. The growth media for the respective cells were used for preparation of the cells and dilution of the viruses. The cells were subjected to a flow cytometer FACS Vantage three days after infection to determine the ratio of rsGFP-expressing cells. The results are shown in FIGS. 2 and 3. FIG. 2 shows the results for K562 cells and FIG. 3 shows the results for TF-1 cells. In the figures, the names of clones from which the virus supernatants were prepared are indicated along the horizontal axis. The longitudinal axis represents the gene transfer efficiency (%).

The ratios of rsGFP-expressing cells for K562 and TF-1 cells infected with the human GnT-III-modified virus were increased by 1.5- to 1.7-fold as compared with the ratios for K562 and TF-1 cells infected with the unmodified virus.

4. Gene Transfer into Various Cells

Cultivation was carried out at 37° C. with 5% $CO_2$ using, as a growth medium, DMEM containing 10% fetal calf serum for HT1080 cells (ATCC CCL-121), 293 cells (ATCC CRL-1573), A375M cells (Cancer Lett., 38:137-147 (1987)), KB cells (ATCC CCL-17) and MDA-MB-435S cells (ATCC HTB-129), or RPMI-1640 containing 10% fetal calf serum for MKN1 cells (BRC RCB1003). Among the virus supernatants prepared in Example 3, the virus prepared from 293T/hG3-1 as a human GnT-III-modified virus and viruses prepared from 293T and 293T/M2 as controls were used. Infection of various cells was carried out as described in "2" above under the conditions of M.O.I.=0.2 using polybrene or a CH-296-coated plate. The respective cells were subjected to a flow cytometer FACS Vantage three days after the infection to determine the ratios of cells expressing rsGFP. The results are shown in FIGS. 4-9. The results for HT1080 cells, 293 cells, A375M cells, KB cells, MDA-MB-435S cells and MKN1 cells are shown in FIGS. 4-9, respectively. In the figures, the names of clones from which the virus supernatants were prepared are indicated along the horizontal axes. (Pb) represents the group of infection in the presence of polybrene, and (RN) represents the group of infection using the CH-296-coated plate. The longitudinal axes represent the gene transfer efficiency (%).

The ratios of rsGFP-expressing cells for the cells infected with the human GnT-III-modified virus were increased as compared with the ratios for the cells infected with the unmodified virus.

Example 5

Preparation of Virus from 293T/hG3 Clone and Gene Transfer into Target Cells

1. Preparation of Virus Supernatant

Among the 293T/hG3 clones isolated in Example 2 for which expression was confirmed, the cell line 293T/hG3-1 was selected, and an amphotropic virus supernatant and an ecotropic virus supernatant were prepared. The same procedures were conducted using 293T cell in control experiments. $3 \times 10^6$ cells of 293T or the 293T/hG3 clone were seeded into a 6-cm tissue culture plate (Iwaki Glass), and cultured overnight in 4 ml of DMEM containing 10% fetal calf serum at 37° C. with 5% $CO_2$. On the next day, it was confirmed that the cells of 293T or the 0.293T/hG3 clone reached semi-confluence, DMEM containing 10% fetal calf serum in the plate was removed by suction, and 3 ml of fresh DMEM containing 10% fetal calf serum was added to each plate. Chloroquin (Wako Pure Chemical Industries) at a final concentration of 25 µM was further added to each plate. The following components were combined in each of two polystyrene round-bottom tubes for preparation of amphotropic retrovirus: 5 µg of a plasmid vector pGP (Takara Bio); 5 µg of a plasmid vector pE-ampho (Takara Bio) for expressing amphotropic env; 10 µg of a plasmid vector for retrovirus production (a retrovirus vector plasmid pDON-AI (Takara Bio) carrying rsGFP gene); 62 µl of 2 M $CaCl_2$; and sterile distilled water to 500 µl. Similarly, the following components were combined in each of two polystyrene round-bottom tubes for preparation of ecotropic retrovirus: 5 µg of a plasmid vector pGP; 5 µg of a plasmid vector pE-eco (Takara Bio) for expressing ecotropic env; 10 µg of a plasmid vector for retrovirus production (a retrovirus vector plasmid PDON-AI carrying rsGFP gene); 62 µl of 2 M $CaCl_2$; and sterile distilled water to 500 µl. Immediately after adding 500 µl of transfection buffer to each tube, the mixture was subjected to bubbling for 20 seconds utilizing excretion from an electric pipetter. 1 ml of the mixture was homogeneously added dropwise to each plate. The plate was incubated at 37° C. with 5% $CO_2$ for 9 hours. After 9 hours, 3 ml of the culture supernatant was removed, 4 ml of fresh DMEM containing 10% fetal calf serum was added to each plate, and the cells were cultured at 37° C. with 5% $CO_2$. The medium in each plate was exchanged for 4 ml of fresh DMEM containing 10% fetal calf serum 24 hours after the transfection. After further culturing at 37° C. with 5% $CO_2$ for 24 hours, the culture supernatant was filtered through a 0.45-µm filter (Millipore), and stored as a virus supernatant stock at −80° C. until use.

2. Measurement of Titer of Virus Supernatant

A titer of a virus supernatant was measured using NIH/3T3 cells as described in "2" (measurement of titer of virus supernatant) of Example 3. The titers of amphotropic retroviruses were $1.9 \times 10^6$ I.V.P./ml (the virus supernatant from the 293/hG3 clone) and $1.1 \times 10^6$ I.V.P./ml (the virus supernatant from 293T cell used in the control experiment). The titers of ecotropic retroviruses were $3.7 \times 10^6$ I.V.P./ml (the virus supernatant from the 293/hG3 clone) and $6.0 \times 10^6$ I.V.P./ml (the virus supernatant from 293T cell used in the control experiment).

3. Gene Transfer Utilizing Human GnT-III-Modified Amphotropic Retrovirus

Figure 10:
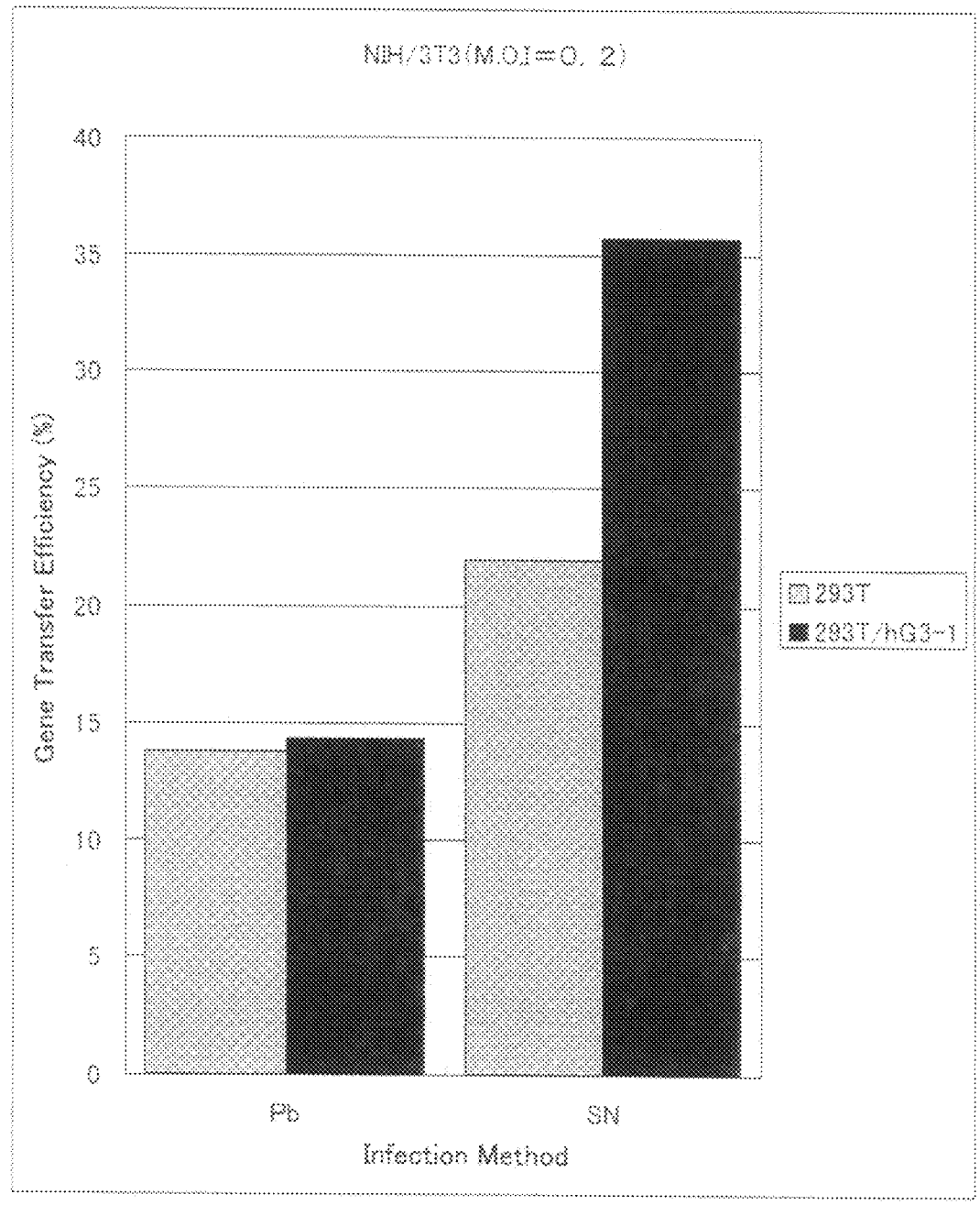
FIG. 10 represents gene transfer efficiencies according to various infection methods using amphotropic retroviruses derived from 293T or a cell line 293T/hG3-1.
Figure 11:
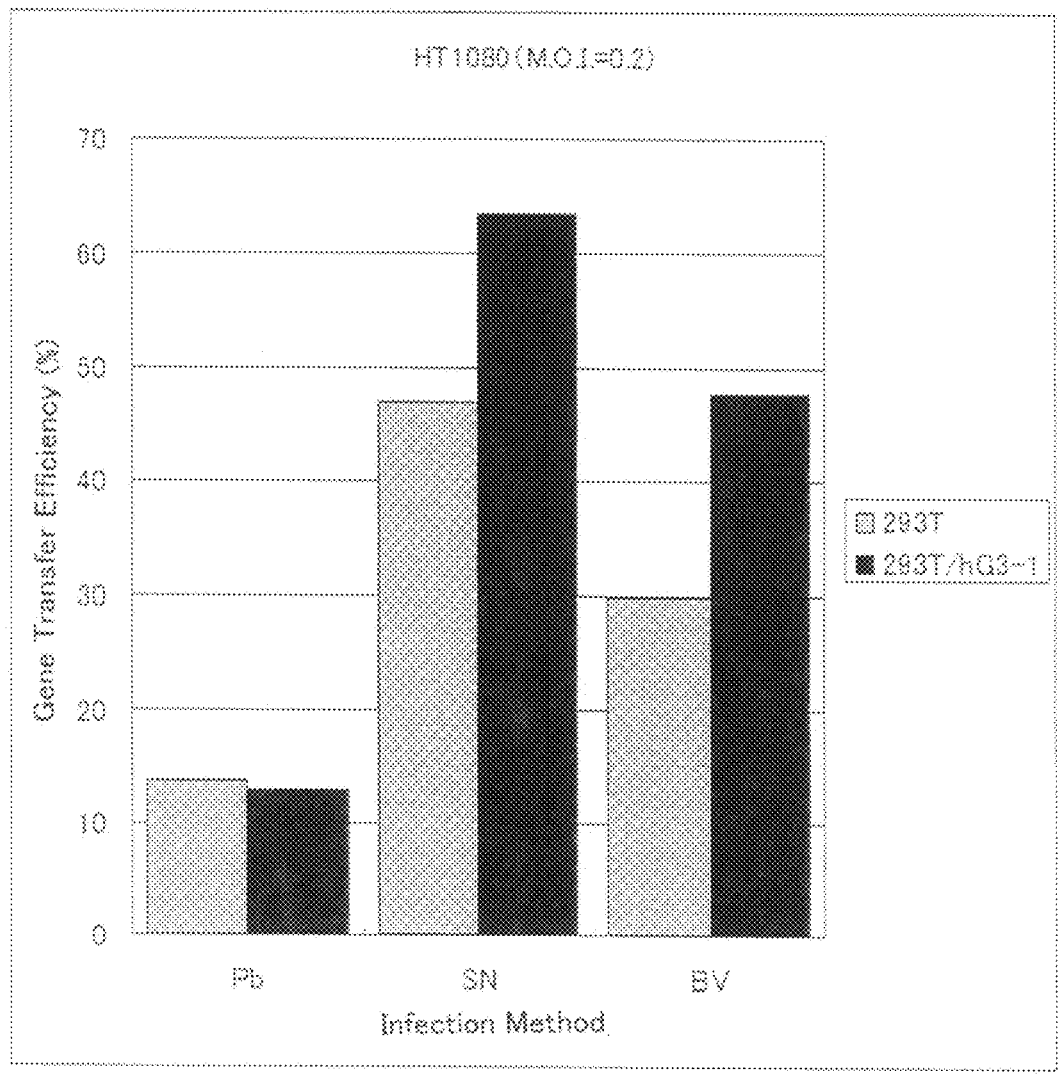
FIG. 11 represents gene transfer efficiencies according to various infection methods using amphotropic retroviruses derived from 293T or a cell line 293T/hG3-1.
Figure 12:
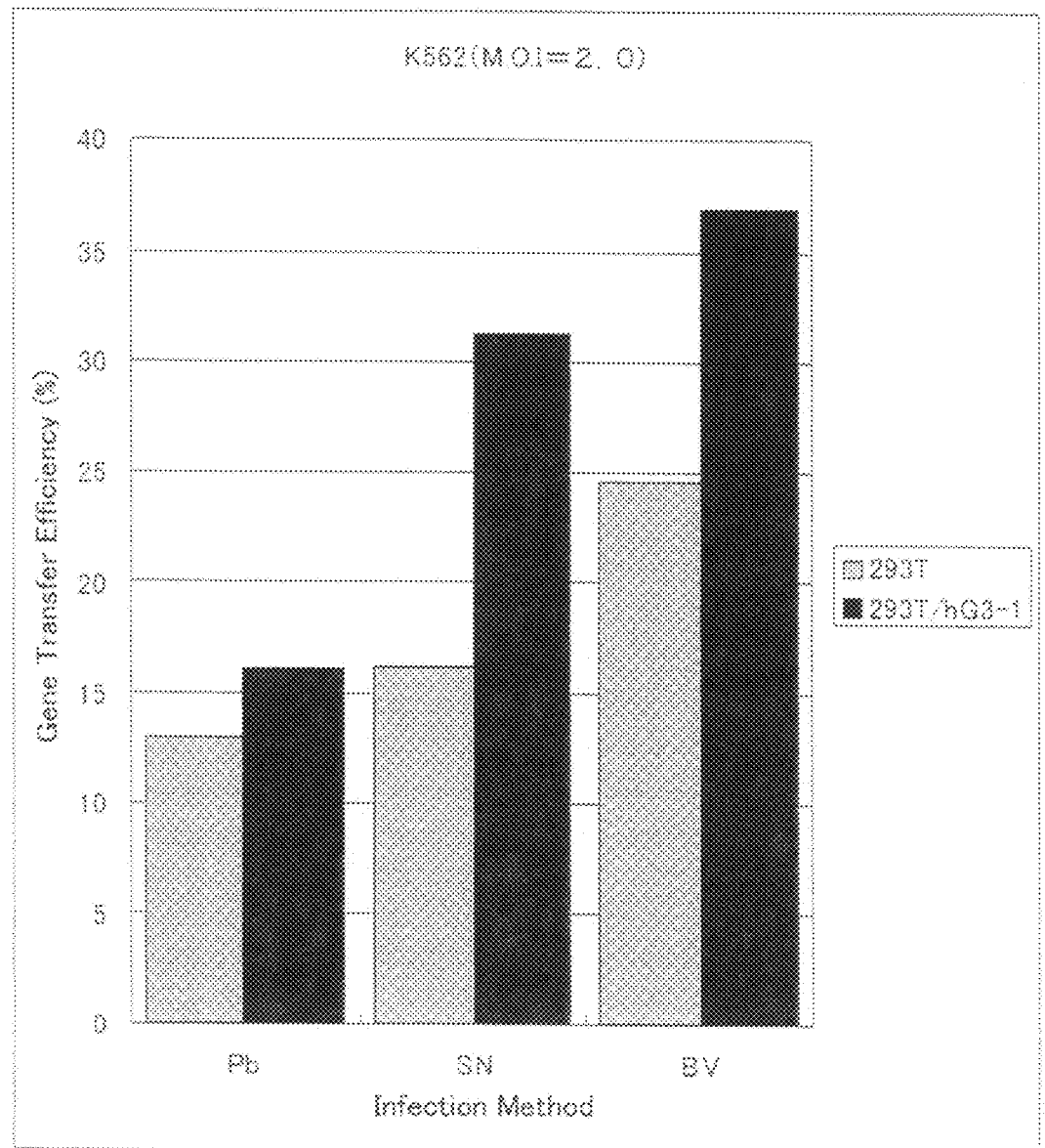
FIG. 12 represents gene transfer efficiencies according to various infection methods using amphotropic retroviruses derived from 293T or a cell line 293T/hG3-1.

Among the virus supernatants prepared in "1" of Example 5, the human GnT-III-modified amphotropic retrovirus prepared using the cell line 293T/hG3-1 and the amphotropic retrovirus prepared using 293T cell as a control were used for gene transfer into NIH/3T3 cells according to a polybrene (Pb) method or a supernatant (SN) method using a CH-296-coated plate under conditions of M.O.I.=0.2. Furthermore, gene transfer into HT1080 cells and K562 cells was carried out according to one of the three methods: the Pb method, the SN method and a bound virus (BV) method using a CH-296-coated plate. In each method, HT1080 cells were infected under conditions of M.O.I.=0.2, and K562 cells were infected under conditions of M.O.I.=2.0. The Pb method and the SN method were carried out according to the methods as described in "2" of Example 4. The BV method was carried out as follows. The virus supernatant was adjusted to $8 \times 10^3$ I.V.P./ml (for infection of HT1080 cells) or $8 \times 10^4$ I.V.P./ml (for infection of K562 cells) using RPMI-1640 containing 10% fetal calf serum, and a 500-µl aliquot was added to each well of a CH-296-coated plate. The plate was then allowed to stand at 37° C. in a 5% $CO_2$ incubator for 4 hours to promote adsorption of the virus to CH-296. After four hours, the virus supernatant was removed, the plate was washed with 0.5 ml/well of 1×PBS, and 500 µl of a cell suspension adjusted to $4 \times 10^4$/ml was added to each well for infection. The cells were cultured at 37° C. with 5% $CO_2$ for three days. After three days, the respective cells were subjected to a flow cytometer FACS Vantage (Becton-Dickinson) to determine the ratios of the cells expressing GFP. The results are shown in FIGS. 10-12. The results for NIH/3T3 cells, HT1080 cells and K562 cells are shown in FIGS. 10-12, respectively. In the figures, the infection methods are indicated along the horizontal axes. Pb represents the group of infection in the presence of polybrene, SN represents the group of infection according to the supernatant method using the CH-296-coated plate, and BV represents the group of infection according to the bound virus method using the CH-296-coated plate. The longitudinal axes represent the gene transfer efficiency (%).

The ratios of rsGFP-expressing cells in the cells infected with the human GnT-III-modified virus in the presence of CH-296 were increased as compared with those in the cells infected with the unmodified virus.

4. Gene Transfer Utilizing Human Gnt-III-Modified Ecotropic Retrovirus

Figure 13:
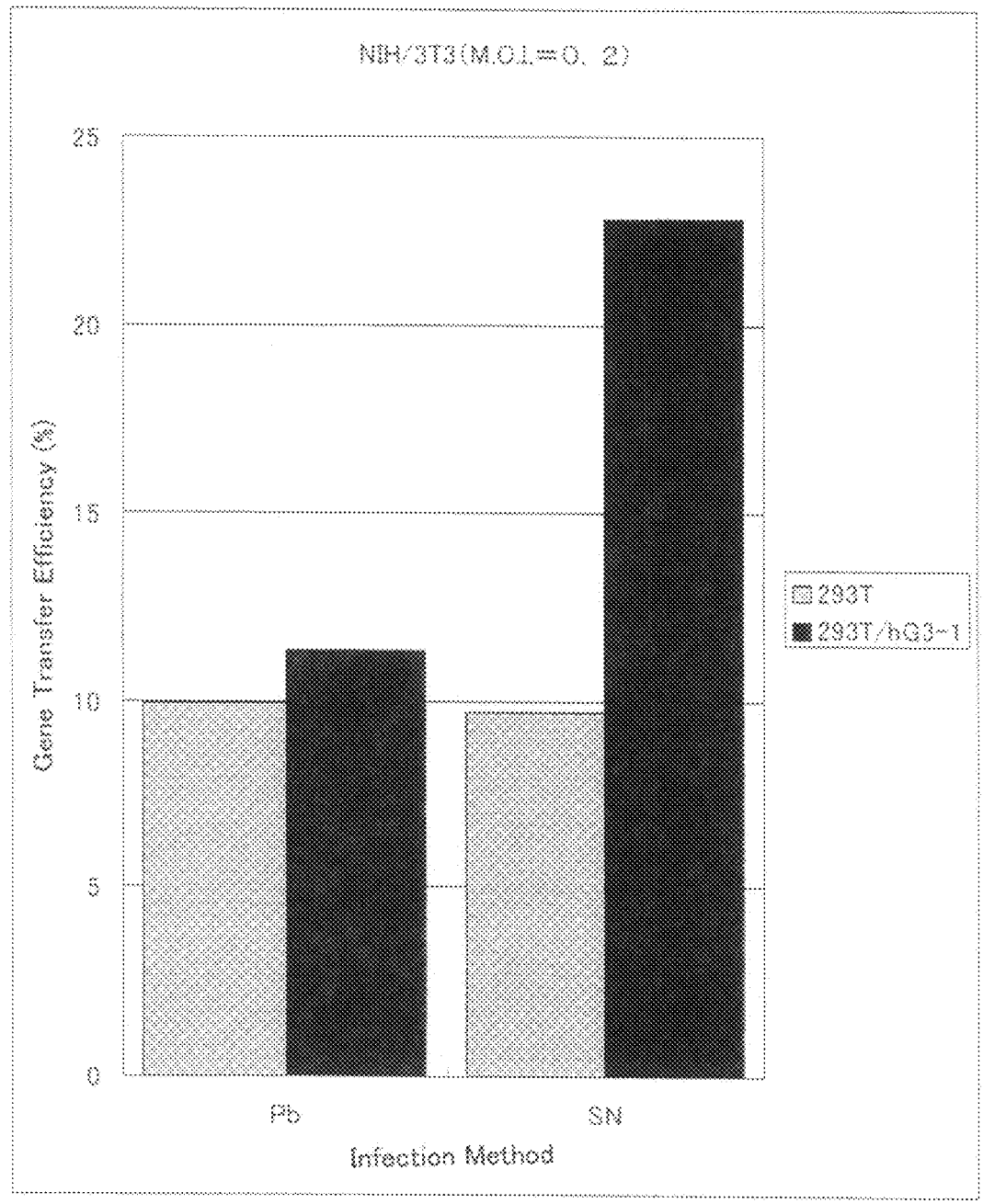
FIG. 13 represents gene transfer efficiencies according to various infection methods using ecotropic retroviruses derived from 293T or a cell line 293T/hG3-1.

Among the virus supernatants prepared in "1" of Example 5, the human GnT-III-modified ecotropic retrovirus prepared using the cell line 293T/hG3-1 and the ecotropic retrovirus prepared using 293T cell as a control were used for gene transfer into NIH/3T3 cells according to the Pb method or the SN method using a CH-296-coated plate under conditions of M.O.I.=0.2. Furthermore, mouse L1210 cells (ATCC CCL-219) were cultured using RPMI-1640 containing 10% fetal calf serum as a growth medium at 37° C. with 5% $CO_2$, and infection was carried out under conditions of M.O.I.=2.0 according to one of three methods: the Pb method, the SN method and the BV method using a CH-296-coated plate. The Pb method and the SN method were carried out according to the methods as described in "2" of Example 4. The BV method was carried out according to the method as described in "3" above. The cells were cultured at 37° C. with 5% $CO_2$ for three days. After three days, the respective cells were subjected to a flow cytometer FACS Vantage (Becton-Dickinson) to determine the ratios of the cells expressing GFP. The results are shown in FIGS. 13 and 14. The results for NIH/3T3 cells and L1210 cells are shown in FIGS. 13 and 14, respectively. In the figures, the infection methods are indicated along the horizontal axes. Pb represents the group of infection in the presence of polybrene, SN represents the group of infection according to the supernatant method using the CH-296-coated plate, and BV represents the group of infection according to the bound virus method using the CH-296-coated plate. The longitudinal axes represent the gene transfer efficiency (%).

The ratios of rsGFP-expressing cells in the cells infected with the human GnT-III-modified virus in the presence of CH-296 were increased as compared with those in the cells infected with the unmodified virus.

INDUSTRIAL APPLICABILITY

The present invention provides a recombinant retrovirus vector which results in high gene transfer efficiency in the presence of a functional substance having a retrovirus-binding activity. By using the vector, a gene of interest can be stably transferred into a target cell with high efficiency. Since a retrovirus vector can be used for treatment of not only genetic diseases but also other various diseases, the present invention is widely useful in the field of medical treatment.

SEQUENCE LISTING FREE TEXT

SEQ ID NO:2; Synthetic primer hG3-F1 to amplify a gene encoding GnT-III.
SEQ ID NO:3; Synthetic primer hG3-R4 to amplify a gene encoding GnT-III.

The invention claimed is:

1. A method for transferring a gene of interest into a target cell, the method comprising:
   (i) increasing the expression or activity of N-acetylglucosaminyltransferase III in a human retrovirus producer cell in vitro;
   (ii) culturing said retrovirus producer cell in vitro, wherein said producer cell has a gag-pol gene and an env gene derived from a retrovirus, and wherein said producer cell is transformed with a recombinant retrovirus or a recombinant retrovirus plasmid vector, wherein said retrovirus or said plasmid vector comprises said gene of interest;
   (iii) collecting a culture supernatant from the culture in (ii) to obtain a retrovirus comprising said gene of interest; and
   (iv) infecting a target cell with the retrovirus of (iii) in the presence of a fibronectin fragment having both a cell adhesion domain and a heparin-binding domain in vitro, wherein the cell adhesion domain comprises a very late antigen (VLA)-5-binding domain and a VLA-4-binding domain.

2. The method according to claim 1, wherein the retrovirus producer cell is transformed with a plasmid containing the gag-pol gene and the env gene derived from the retrovirus.

3. The method according to claim 1, wherein the producer cell is derived from a cell selected from the group consisting of a 293 cell and a 293T cell.

4. The method according to claim 1, wherein said increasing of expression or activity of N-acetylglucosaminyltransferase III in step (i) is obtained by transfer of an N-acetylglucosaminyltransferase III gene into said producer cell.

5. The method according to claim 4, wherein the N-acetylglucosaminyltransferase III activity is increased by integration of the N-acetylglucosaminyltransferase III gene into a chromosome of said producer cell.

6. The method according to claim 4, wherein the N-acetylglucosaminyltransferase III activity is increased by transformation of said producer cell with a plasmid vector containing the N-acetylglucosaminyltransferase III gene.

7. The method according to claim 4, wherein the N-acetylglucosaminyltransferase III gene in said producer cell is placed under control of a heterologous promoter.

8. A method for transferring a gene of interest into a target cell, the method comprising:
   (i) increasing the expression or activity of N-acetylglucosaminyltransferase III in a human retrovirus producer cell in vitro;
   (ii) culturing said retrovirus producer cell in vitro, wherein said producer cell has a gag-pol gene and an env gene derived from a retrovirus, and wherein said producer cell is transformed with a recombinant retrovirus or a recombinant retrovirus plasmid vector, wherein said retrovirus or said plasmid vector comprises said gene of interest;
   (iii) collecting a culture supernatant from the culture in (ii) to obtain a retrovirus comprising said gene of interest; and
   (iv) infecting a target cell with the retrovirus of (iii) in the presence of a fibronectin fragment having both a cell adhesion domain and a heparin-binding domain in vitro, wherein the cell adhesion domain comprises a very late antigen (VLA)-5-binding domain and a VLA-4-binding domain, wherein the efficiency of infection of said target cell with said retrovirus is greater than that achieved if said N-acetylglucosaminyltransferase III activity is not increased in said producer cell, and is also greater than that achieved if said target cell is infected in the presence of polybrene instead of said fibronectin fragment.

* * * * *

SEQUENCE LISTING

```
<160> NUMBER OF SEQ ID NOS: 3

<210> SEQ ID NO 1
<211> LENGTH: 1593
<212> TYPE: DNA
<213> ORGANISM: Homo sapiens

<400> SEQUENCE: 1
atgagacgct acaagctctt tctcatgttc tgtatggccg gcctgtgcct catctccttc      60
ctgcacttct tcaagaccct gtcctatgtc accttccccc gagaactggc ctccctcagc     120
cctaacctgg tgtccagctt tttctggaac aatgcccccgg tcacgcccca ggccagcccc    180
gagccaggag gccctgacct gctgcgtacc ccactctact cccactcgcc cctgctgcag    240
ccgctgccgc ccagcaaggc ggccgaggag ctccaccggg tggacttggt gctgcccgag    300
gacaccaccg agtatttcgt gcgcaccaag gccggcggcg tctgcttcaa acccggcacc    360
aagatgctgg agaggccgcc cccgggacgg ccggaggaga agcctgaggg ggccaacggc    420
tcctcggccc ggcggccacc ccggtacctc ctgagcgccc gggagcgcac gggggggccga    480 ggcgcccggc gcaagtgggt ggagtgcgtg tgcctgcccg gctggacgg acccagctgc    540 ggcgtgccca ctgtggtgca gtactccaac ctgcccacca aggagcggct ggtgcccagg    600
gaggtgccgc gccgcgtcat caacgccatc aacgtcaacc acgagttcga cctgctggac    660
gtgcgcttcc acgagctggg cgacgtggtg gacgcctttg tggtgtgcga gtccaacttc    720
acggcttatg gggagccgcg gccgctcaag ttccgggaga tgctgaccaa tggcaccttc    780
gagtacatcc gccacaaggt gctctatgtc ttcctggacc acttcccgcc cggcggccgg    840
caggacggct ggatcgccga cgactacctg cgcaccttcc tcacccagga cggcgtctcg    900
cggctgcgca acctgcggcc cgacgacgtc ttcatcattg acgatgcgga cgagatcccg    960
gcccgtgacg gcgtcctttt cctcaagctc tacgatggct ggaccgagcc cttcgccttc    1020
cacatgcgca cgtcgctcta cggcttcttc tggaagcagc cgggcacccct ggaggtggta   1080 tcaggctgca cggtggacat gctgcaggca gtgtatgggc tggacggcat ccgcctgcgc   1140
```

```
cgccgccagt actacaccat gcccaacttc agacagtatg agaaccgcac cggccacatc    1200
ctggtgcagt ggtcgctggg cagcccctg cacttcgccg gctggcactg ctcctggtgc    1260
ttcacgcccg agggcatcta cttcaagctc gtgtccgccc agaatggcga cttcccacgc    1320
tggggtgact acgaggacaa gcgggacctg aactacatcc gcggcctgat ccgcaccggg    1380
ggctggttcg acggcacgca gcaggagtac ccgcctgcag accccagcga gcacatgtat    1440
gcgcccaagt acctgctgaa gaactacgac cggttccact acctgctgga caacccctac    1500
caggagccca ggagcacggc ggcgggcggg tggcgccaca ggggtcccga gggaaggccg    1560
cccgcccggg gcaaactgga cgaggcggaa gtc                                  1593

<210> SEQ ID NO 2
<211> LENGTH: 28
<212> TYPE: DNA
<213> ORGANISM: Artificial sequence
<220> FEATURE:
<223> OTHER INFORMATION: Synthetic primer hG3-F1 to amplify a gene
      encoding GnT-III.

<400> SEQUENCE: 2
aaccatggcg atgagacgct acaagctc                                          28

<210> SEQ ID NO 3
<211> LENGTH: 20
<212> TYPE: DNA
<213> ORGANISM: Artificial sequence
<220> FEATURE:
<223> OTHER INFORMATION: Synthetic primer hG3-R4 to amplify a gene
      encoding GnT-III.

<400> SEQUENCE: 3
ctctccagca tcttggtgcc                                                   20
```